(12) United States Patent
Yoshida et al.

(10) Patent No.: US 11,932,896 B2
(45) Date of Patent: Mar. 19, 2024

(54) HOST CELLS AND METHODS FOR PRODUCING HYDROXYTYROSOL

(71) Applicant: The Regents of the University of California, Oakland, CA (US)

(72) Inventors: Erika Yoshida, Tokyo (JP); Taek Soon Lee, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/232,614

(22) Filed: Dec. 26, 2018

(65) Prior Publication Data
US 2019/0194698 A1 Jun. 27, 2019

Related U.S. Application Data

(63) Continuation of application No. PCT/US2017/039329, filed on Jun. 26, 2017.

(60) Provisional application No. 62/354,657, filed on Jun. 24, 2016.

(51) Int. Cl.
*C12P 7/22* (2006.01)
*C12N 15/52* (2006.01)
*C12P 13/22* (2006.01)

(52) U.S. Cl.
CPC ............. *C12P 7/22* (2013.01); *C12N 15/52* (2013.01); *C12P 13/22* (2013.01); *C12N 2510/02* (2013.01)

(58) Field of Classification Search
None
See application file for complete search history.

(56) References Cited

U.S. PATENT DOCUMENTS

| | | | | |
|---|---|---|---|---|
| 10,023,889 B2 * | 7/2018 | Yan | ............. | A23L 2/52 |
| 10,100,342 B2 * | 10/2018 | Lynch | ............. | C12N 15/63 |
| 10,597,685 B2 * | 3/2020 | Lee | ............. | C12P 7/22 |
| 10,612,006 B2 * | 4/2020 | Fukui | ............. | C12N 9/0006 |
| 10,851,365 B2 * | 12/2020 | Luo | ............. | C12N 1/14 |
| 2010/0068775 A1 | 3/2010 | Achkar et al. | | |
| 2014/0134689 A1 | 5/2014 | Lee et al. | | |
| 2016/0060638 A1 | 3/2016 | Yan et al. | | |

OTHER PUBLICATIONS

Satoh et al. (Metabolic Eng., vol. 14, 2012, pp. 603-610).*
International Search Report and Written Opinion for PCT/US2017/039329, dated Oct. 24, 2017, 8 pages.
Satoh, et al., "Engineering of L-tyrosine oxidation in *Escherichia coli* and microbial production of hydroxytyrosol," Metabolic Engineering, 2012, vol. 14, No. 6, pp. 603-610.
Juminaga, et al., "Modular Engineering of L-Tyrosine Production in *Escherichia coli*," Applied and Environmental Microbiology, Jan. 2012, vol. 78, No. 1, pp. 89-98.
Extended European Search Report, European Patent App. No. 17816378.8, dated Mar. 6, 2020, 12 pp.

* cited by examiner

*Primary Examiner* — Hope A Robinson
(74) *Attorney, Agent, or Firm* — Kilpatrick Townsend & Stockton LLP

(57) ABSTRACT

The present invention provides for a composition comprising: (a) a first host cell capable of producing L-DOPA; and (b) a modified host cell is capable of converting L-DOPA into hydroxytyrosol (HTy); wherein any one or both of the first host cell and second host cell is a genetically modified host cell.

6 Claims, 8 Drawing Sheets

Specification includes a Sequence Listing.

SEQUENCE LISTING

<160> NUMBER OF SEQ ID NOS: 8

<210> SEQ ID NO 1
<211> LENGTH: 498
<212> TYPE: PRT
<213> ORGANISM: Mus musculus

<400> SEQUENCE: 1

Met Pro Thr Pro Ser Ala Ser Ser Pro Gln Pro Lys Gly Phe Arg Arg
1               5                   10                  15

```
Ala Val Ser Glu Gln Asp Thr Lys Gln Ala Glu Val Thr Ser Pro
             20                  25                  30

Arg Phe Ile Gly Arg Arg Gln Ser Leu Ile Glu Asp Ala Arg Lys Glu
         35                  40                  45

Arg Glu Ala Ala Ala Ala Ala Ala Ala Ala Val Ala Ser Ala Glu
 50                  55                  60

Pro Gly Asn Pro Leu Glu Ala Val Val Phe Glu Glu Arg Asp Gly Asn
 65                  70                  75                  80

Ala Val Leu Asn Leu Leu Phe Ser Leu Arg Gly Thr Lys Pro Ser Ser
                 85                  90                  95

Leu Ser Arg Ala Leu Lys Val Phe Glu Thr Phe Glu Ala Lys Ile His
             100                 105                 110

His Leu Glu Thr Arg Pro Ala Gln Arg Pro Leu Ala Gly Ser Pro His
         115                 120                 125

Leu Glu Tyr Phe Val Arg Phe Glu Val Pro Ser Gly Asp Leu Ala Ala
 130                 135                 140

Leu Leu Ser Ser Val Arg Arg Val Ser Asp Asp Val Arg Ser Ala Arg
145                 150                 155                 160

Glu Asp Lys Val Pro Trp Phe Pro Arg Lys Val Ser Glu Leu Asp Lys
                165                 170                 175

Cys His His Leu Val Thr Lys Phe Asp Pro Asp Leu Asp Leu Asp His
             180                 185                 190

Pro Gly Phe Ser Asp Gln Ala Tyr Arg Gln Arg Arg Lys Leu Ile Ala
         195                 200                 205

Glu Ile Ala Phe Gln Tyr Lys Gln Gly Glu Pro Ile Pro His Val Glu
 210                 215                 220

Tyr Thr Lys Glu Glu Ile Ala Thr Trp Lys Glu Val Tyr Ala Thr Leu
225                 230                 235                 240

Lys Gly Leu Tyr Ala Thr His Ala Cys Arg Glu His Leu Glu Ala Phe
                245                 250                 255

Gln Leu Leu Glu Arg Tyr Cys Gly Tyr Arg Glu Asp Ser Ile Pro Gln
            260                 265                 270

Leu Glu Asp Val Ser His Phe Leu Lys Glu Arg Thr Gly Phe Gln Leu
        275                 280                 285

Arg Pro Val Ala Gly Leu Leu Ser Ala Arg Asp Phe Leu Ala Ser Leu
290                 295                 300

Ala Phe Arg Val Phe Gln Cys Thr Gln Tyr Ile Arg His Ala Ser Ser
305                 310                 315                 320

Pro Met His Ser Pro Glu Pro Asp Cys Cys His Glu Leu Leu Gly His
                325                 330                 335

Val Pro Met Leu Ala Asp Arg Thr Phe Ala Gln Phe Ser Gln Asp Ile
            340                 345                 350

Gly Leu Ala Ser Leu Gly Ala Ser Asp Glu Glu Ile Glu Lys Leu Ser
        355                 360                 365

Thr Val Tyr Trp Phe Thr Val Glu Phe Gly Leu Cys Lys Gln Asn Gly
370                 375                 380

Glu Leu Lys Ala Tyr Gly Ala Gly Leu Leu Ser Ser Tyr Gly Glu Leu
385                 390                 395                 400

Leu His Ser Leu Ser Glu Glu Pro Glu Val Arg Ala Phe Asp Pro Asp
                405                 410                 415

Thr Ala Ala Val Gln Pro Tyr Gln Asp Gln Thr Tyr Gln Pro Val Tyr
            420                 425                 430
```

```
Phe Val Ser Glu Ser Phe Ser Asp Ala Lys Asp Lys Leu Arg Asn Tyr
            435                 440                 445
Ala Ser Arg Ile Gln Arg Pro Phe Ser Val Lys Phe Asp Pro Tyr Thr
            450                 455                 460
Leu Ala Ile Asp Val Leu Asp Ser Pro His Thr Ile Arg Arg Ser Leu
465                 470                 475                 480
Glu Gly Val Gln Asp Glu Leu His Thr Leu Thr Gln Ala Leu Ser Ala
                    485                 490                 495
Ile Ser

<210> SEQ ID NO 2
<211> LENGTH: 104
<212> TYPE: PRT
<213> ORGANISM: Homo sapiens

<400> SEQUENCE: 2

Met Ala Gly Lys Ala His Arg Leu Ser Ala Glu Glu Arg Asp Gln Leu
1               5                   10                  15
Leu Pro Asn Leu Arg Ala Val Gly Trp Asn Glu Leu Glu Gly Arg Asp
                20                  25                  30
Ala Ile Phe Lys Gln Phe His Phe Lys Asp Phe Asn Arg Ala Phe Gly
            35                  40                  45
Phe Met Thr Arg Val Ala Leu Gln Ala Glu Lys Leu Asp His His Pro
50                  55                  60
Glu Trp Phe Asn Val Tyr Asn Lys Val His Ile Thr Leu Ser Thr His
65                  70                  75                  80
Glu Cys Ala Gly Leu Ser Glu Arg Asp Ile Asn Leu Ala Ser Phe Ile
                85                  90                  95
Glu Gln Val Ala Val Ser Met Thr
                100

<210> SEQ ID NO 3
<211> LENGTH: 244
<212> TYPE: PRT
<213> ORGANISM: Homo sapiens

<400> SEQUENCE: 3

Met Ala Ala Ala Ala Ala Gly Glu Ala Arg Arg Val Leu Val Tyr
1               5                   10                  15
Gly Gly Arg Gly Ala Leu Gly Ser Arg Cys Val Gln Ala Phe Arg Ala
                20                  25                  30
Arg Asn Trp Trp Val Ala Ser Val Asp Val Val Glu Asn Glu Glu Ala
            35                  40                  45
Ser Ala Ser Ile Ile Val Lys Met Thr Asp Ser Phe Thr Glu Gln Ala
            50                  55                  60
Asp Gln Val Thr Ala Glu Val Gly Lys Leu Leu Gly Glu Glu Lys Val
65                  70                  75                  80
Asp Ala Ile Leu Cys Val Ala Gly Gly Trp Ala Gly Gly Asn Ala Lys
                85                  90                  95
Ser Lys Ser Leu Phe Lys Asn Cys Asp Leu Met Trp Lys Gln Ser Ile
                100                 105                 110
Trp Thr Ser Thr Ile Ser Ser His Leu Ala Thr Lys His Leu Lys Glu
            115                 120                 125
Gly Gly Leu Leu Thr Leu Ala Gly Ala Lys Ala Ala Leu Asp Gly Thr
130                 135                 140
```

```
Pro Gly Met Ile Gly Tyr Gly Met Ala Lys Gly Ala Val His Gln Leu
145                 150                 155                 160

Cys Gln Ser Leu Ala Gly Lys Asn Ser Gly Met Pro Pro Gly Ala Ala
                165                 170                 175

Ala Ile Ala Val Leu Pro Val Thr Leu Asp Thr Pro Met Asn Arg Lys
                180                 185                 190

Ser Met Pro Glu Ala Asp Phe Ser Ser Trp Thr Pro Leu Glu Phe Leu
            195                 200                 205

Val Glu Thr Phe His Asp Trp Ile Thr Gly Lys Asn Arg Pro Ser Ser
            210                 215                 220

Gly Ser Leu Ile Gln Val Val Thr Thr Glu Gly Arg Thr Glu Leu Thr
225                 230                 235                 240

Pro Ala Tyr Phe
```

<210> SEQ ID NO 4
<211> LENGTH: 1860
<212> TYPE: DNA
<213> ORGANISM: Sus scrofa

<400> SEQUENCE: 4

```
gaattcacat atgaatgcca gcgatttccg tcgacgcggc aaagaaatgg tggattacat    60
ggcggattac ctggaaggca tcgaaggtcg tcaggtgtac ccggatgtgc agccggggta   120
cctgcgtccg ctgatcccgg cgaccgcccc gcaggaaccg gataccttcg aagatatcct   180
gcaggatgtg gaaaaaatca tcatgccggg gtgacccact ggcacagccc gtacttcttc   240
gcgtacttcc cgaccgccag cagctacccg gcgatgctgg cggatatgct gtgcggtgcg   300
atcggatgca tcggtttcag ctgggcggct agcccggcgt gcaccgaact cgagaccgtg   360
atgatggatt ggctgggcaa aatgctccag cttccggaag cgttcctggc gggcgaagcc   420
ggtgaaggcg gcggcgtgat ccagggtagc gccagcgaag ccaccctggt ggcgctgctg   480
gcggcgcgta ccaaagtggt gcgacgtctg caagcggcga gcccgggcct gacccagggc   540
gcggtgctgg aaaaactagt ggcgtacgcg agtgatcagg cgcacagcag cgtggaacgt   600
gccggcctga tcgcggcgt gaaactgaaa gcgatcccga gcgatggcaa attcgcgatg   660
cgtgcgagcg cgctgcagga ggccctggag agagacaagg ctgccggcct gattcctttc   720
ttcgtggtgg ctacgctggg gaccacatcg tgctgctcct tgacaatctc ttagaagtg    780
ggacccatct gtcacgaaga ggacatatgg ctgcacgtgg atgctgccta cgcaggcagt   840
gccttcatct gccctgagtt ccggcacctg ctgaatggag tggagtttgc agattcattt   900
aactttaatc cccacaaatg gctcttggtg aattttgact gctcggctat gtgggtgaaa   960
aggagaacgg acctgactgg agccttcaaa ttggaccccg tgtacttaaa gcacagccac  1020
cagggctcgg ggcttatcac ggactacagg cactggcagc tgccactggg tcggcgattc  1080
cggtccctga aaatgtggtt tgttttttagg atgtacggag tcaagggact gcaggcctat  1140
atccgcaagc acgtgcagct gtctcatgag tttgaggcat ttgtgcttca ggatccacgc  1200
tttgaagtct gtgccgaagt caccctgggg ctggtgtgtt tccggctgaa gggctccgac  1260
ggactgaatg aagcgcttct ggaaaggata aacagcgcca ggaaaatcca cttggttccc  1320
tgtcgcctga ggggccagtt cgtgctgcgg ttcgccatct gctcgcgcaa ggtggagtcg  1380
ggccacgtgc ggctggcctg ggagcacatc cgagggctgg cggccgagct gctggccgcg  1440
gaggagggaa aggcagagat caaaagttga agtgccctga agagcagaat cggaggagac  1500
gcgtcgtccc cgctccgagg cgtagagcct gcaatggtcc ccccagttct ttcagcccac  1560
```

-continued

```
gttctccaga aagaagcttg tgcctacgtc tgaccagcct ctcagcaatg aagaagtatt  1620
atttgctctt tgaaaagtta atcccagtgg agacagcttt tactctttat ttggctgtga  1680
ttgtttgttg attaaaacat cataggtttc tgcatccttg aagttgtcag cggtggtcca  1740
ctttccgggg caacctatgc tgatgggatt tgagagtgat acccgtggtc tttaaattac  1800
tctgtcctgt ggcttatgct taataaatga tgtgaagtgt aaaaaaaaaa aaaaaaaaaa  1860
```

<210> SEQ ID NO 5
<211> LENGTH: 486
<212> TYPE: PRT
<213> ORGANISM: Sus scrofa

<400> SEQUENCE: 5

```
Met Asn Ala Ser Asp Phe Arg Arg Gly Lys Glu Met Val Asp Tyr
1               5                   10                  15

Met Ala Asp Tyr Leu Glu Gly Ile Glu Gly Arg Gln Val Tyr Pro Asp
                20                  25                  30

Val Gln Pro Gly Tyr Leu Arg Pro Leu Ile Pro Ala Thr Ala Pro Gln
            35                  40                  45

Glu Pro Asp Thr Phe Glu Asp Ile Leu Gln Asp Val Glu Lys Ile Ile
    50                  55                  60

Met Pro Gly Val Thr His Trp His Ser Pro Tyr Phe Phe Ala Tyr Phe
65                  70                  75                  80

Pro Thr Ala Ser Ser Tyr Pro Ala Met Leu Ala Asp Met Leu Cys Gly
                85                  90                  95

Ala Ile Gly Cys Ile Gly Phe Ser Trp Ala Ala Ser Pro Ala Cys Thr
            100                 105                 110

Glu Leu Glu Thr Val Met Met Asp Trp Leu Gly Lys Met Leu Gln Leu
        115                 120                 125

Pro Glu Ala Phe Leu Ala Gly Glu Ala Gly Glu Gly Gly Val Ile
    130                 135                 140

Gln Gly Ser Ala Ser Glu Ala Thr Leu Val Ala Leu Leu Ala Ala Arg
145                 150                 155                 160

Thr Lys Val Val Arg Arg Leu Gln Ala Ala Ser Pro Gly Leu Thr Gln
                165                 170                 175

Gly Ala Val Leu Glu Lys Leu Val Ala Tyr Ala Ser Asp Gln Ala His
            180                 185                 190

Ser Ser Val Glu Arg Ala Gly Leu Ile Gly Gly Val Lys Leu Lys Ala
        195                 200                 205

Ile Pro Ser Asp Gly Lys Phe Ala Met Arg Ala Ser Ala Leu Gln Glu
    210                 215                 220

Ala Leu Glu Arg Asp Lys Ala Ala Gly Leu Ile Pro Phe Phe Val Val
225                 230                 235                 240

Ala Thr Leu Gly Thr Thr Ser Cys Cys Ser Phe Asp Asn Leu Leu Glu
                245                 250                 255

Val Gly Pro Ile Cys His Glu Glu Asp Ile Trp Leu His Val Asp Ala
            260                 265                 270

Ala Tyr Ala Gly Ser Ala Phe Ile Cys Pro Glu Phe Arg His Leu Leu
        275                 280                 285

Asn Gly Val Glu Phe Ala Asp Ser Phe Asn Phe Asn Pro His Lys Trp
    290                 295                 300

Leu Leu Val Asn Phe Asp Cys Ser Ala Met Trp Val Lys Arg Arg Thr
305                 310                 315                 320
```

```
Asp Leu Thr Gly Ala Phe Lys Leu Asp Pro Val Tyr Leu Lys His Ser
                325                 330                 335

His Gln Gly Ser Gly Leu Ile Thr Asp Tyr Arg His Trp Gln Leu Pro
            340                 345                 350

Leu Gly Arg Arg Phe Arg Ser Leu Lys Met Trp Phe Val Phe Arg Met
        355                 360                 365

Tyr Gly Val Lys Gly Leu Gln Ala Tyr Ile Arg Lys His Val Gln Leu
    370                 375                 380

Ser His Glu Phe Glu Ala Phe Val Leu Gln Asp Pro Arg Phe Glu Val
385                 390                 395                 400

Cys Ala Glu Val Thr Leu Gly Leu Val Cys Phe Arg Leu Lys Gly Ser
                405                 410                 415

Asp Gly Leu Asn Glu Ala Leu Leu Glu Arg Ile Asn Ser Ala Arg Lys
            420                 425                 430

Ile His Leu Val Pro Cys Arg Leu Arg Gly Gln Phe Val Leu Arg Phe
        435                 440                 445

Ala Ile Cys Ser Arg Lys Val Glu Ser Gly His Val Arg Leu Ala Trp
    450                 455                 460

Glu His Ile Arg Gly Leu Ala Ala Glu Leu Leu Ala Ala Glu Glu Gly
465                 470                 475                 480

Lys Ala Glu Ile Lys Ser
                485

<210> SEQ ID NO 6
<211> LENGTH: 510
<212> TYPE: PRT
<213> ORGANISM: Micrococcus luteus

<400> SEQUENCE: 6

Met Thr Thr Ala Pro Ala Thr Ala Gly Arg Glu Arg Arg Thr Ser Asp
1               5                   10                  15

Val Val Val Ile Gly Ala Gly Pro Ala Gly Leu Met Ala Ala Arg Thr
                20                  25                  30

Ala Lys Ala Gln Gly Leu Ser Val Thr Val Leu Glu Ala Arg Arg Arg
            35                  40                  45

Val Gly Gly Arg Thr Trp Asn Gly Leu Val Glu Gly Ala Asp Gly Lys
        50                  55                  60

Asp His Phe Ile Glu Ile Gly Gly Gln Trp Ile Ser Pro Asp Gln Thr
65                  70                  75                  80

Arg Leu Ile Ser Leu Val Glu Glu Leu Gly Leu Pro Thr Phe Ser Arg
                85                  90                  95

Phe Arg Asp Gly Arg Asn Val Tyr Val Asp Pro Arg Gly Glu Arg His
            100                 105                 110

Val Tyr Asp Gly Leu Asp Phe Pro Val Ala Glu Lys Thr Asp Arg Glu
        115                 120                 125

Met Asp Arg Leu Ile Ala Lys Ile Asp Glu Leu Thr Ala Glu Ile Asp
    130                 135                 140

Ala Ala Pro Trp Glu His Pro Arg Ala Ala Glu Leu Asp Thr Ile
145                 150                 155                 160

Ser Phe Arg His Trp Leu Glu Gln Glu Ser Asp Asp Pro Glu Ala Ile
                165                 170                 175

Asp Asn Val Ser Ile Tyr Ile Ala Ser Gly Met Leu Thr Lys Pro Ser
            180                 185                 190

His Thr Phe Ser Met Leu Gln Ala Leu Leu Met Ala Ala Ser Ala Gly
        195                 200                 205
```

```
Ser Phe Arg Asn Leu Val Asp Glu Asp Phe Ile Leu Asp Lys Arg Val
    210                 215                 220

Glu Gly Gly Met Gln Ser Val Ser Leu Thr Met Ala Ala Glu Leu Gly
225                 230                 235                 240

Asp Asp Val Val Leu Gly Gln Pro Val Arg Thr Leu Arg Trp Ala Glu
                245                 250                 255

Pro Asp Pro Ser Thr Ala Asp Glu Lys Asn Gly Val Ala Ala Asp Val
            260                 265                 270

Arg Asn Gly Val Ala His Asp Gly Ala Ala Gly Asp Val Val Ala Leu
                275                 280                 285

Thr Asp Asp Tyr Glu Val His Ala Arg Tyr Ala Val Leu Ala Val Pro
    290                 295                 300

Pro Asn Leu Tyr Ser Arg Ile Ser Phe Glu Pro Pro Met Pro Arg Glu
305                 310                 315                 320

Gln Gln Ile Ala His Gln His Ile Ser Met Gly Leu Val Ile Lys Val
                325                 330                 335

His Ala Val Tyr Glu Thr Pro Phe Trp Arg Glu Gly Leu Ser Gly
                340                 345                 350

Thr Cys Phe Gly Gly Gly Arg Leu Val Gln Glu Ile Tyr Asp Asn Thr
        355                 360                 365

Asn Arg Gly Glu Asn Leu Ala Gly Gly Ala Pro Gly Glu Glu Asp Pro
    370                 375                 380

His Gly Thr Leu Val Gly Phe Val Ser Asp Val Tyr Ala Glu Gln Met
385                 390                 395                 400

Trp Ala Leu Pro Glu Glu Arg Lys Ala Ala Ile Leu Gly Ala Met
                405                 410                 415

Ala Glu Tyr Leu Gly Pro Arg Thr Leu Glu Pro Ile Ala Phe Phe Leu
                420                 425                 430

Ser Asp Met Ala Ala Glu Glu Trp Thr Arg Gly Ala Tyr Ala Thr Ser
            435                 440                 445

Tyr Asp Leu Gly Gly Leu Ser Arg Trp Gly His Leu Gln Asn Arg Pro
    450                 455                 460

Thr Gly Pro Ile His Tyr Ala Cys Ser Asp Ile Ala Ala Glu Gly Tyr
465                 470                 475                 480

Gln His Val Asp Gly Ala Ile Arg Met Gly Glu Ala Ala Leu Ala
                485                 490                 495

Ile Ala Glu Arg Glu Ala Thr Asp Ala Gly Gln Pro Thr Gly
                500                 505                 510

<210> SEQ ID NO 7
<211> LENGTH: 350
<212> TYPE: PRT
<213> ORGANISM: Escherichia coli

<400> SEQUENCE: 7

Met Asn Tyr Gln Asn Asp Asp Leu Arg Ile Lys Glu Ile Lys Glu Leu
1               5                   10                  15

Leu Pro Pro Val Ala Leu Leu Glu Lys Phe Pro Ala Thr Glu Asn Ala
                20                  25                  30

Ala Asn Thr Val Ala His Ala Arg Lys Ala Ile His Lys Ile Leu Lys
            35                  40                  45

Gly Asn Asp Asp Arg Leu Leu Val Ile Gly Pro Cys Ser Ile His
        50                  55                  60

Asp Pro Val Ala Ala Lys Glu Tyr Ala Thr Arg Leu Leu Ala Leu Arg
65                  70                  75                  80
```

```
Glu Glu Leu Lys Asp Glu Leu Glu Ile Val Met Arg Val Tyr Phe Glu
            85                  90                  95

Lys Pro Arg Thr Thr Val Gly Trp Lys Gly Leu Ile Asn Asp Pro His
        100                 105                 110

Met Asp Asn Ser Phe Gln Ile Asn Asp Gly Leu Arg Ile Ala Arg Lys
        115                 120                 125

Leu Leu Leu Asp Ile Asn Asp Ser Gly Leu Pro Ala Ala Gly Glu Phe
130                 135                 140

Leu Asp Met Ile Thr Pro Gln Tyr Leu Ala Asp Leu Met Ser Trp Gly
145                 150                 155                 160

Ala Ile Gly Ala Arg Thr Thr Glu Ser Gln Val His Arg Glu Leu Ala
                165                 170                 175

Ser Gly Leu Ser Cys Pro Val Gly Phe Lys Asn Gly Thr Asp Gly Thr
                180                 185                 190

Ile Lys Val Ala Ile Asp Ala Ile Asn Ala Ala Gly Ala Pro His Cys
        195                 200                 205

Phe Leu Ser Val Thr Lys Trp Gly His Ser Ala Ile Val Asn Thr Ser
210                 215                 220

Gly Asn Gly Asp Cys His Ile Ile Leu Arg Gly Gly Lys Glu Pro Asn
225                 230                 235                 240

Tyr Ser Ala Lys His Val Ala Glu Val Lys Glu Gly Leu Asn Lys Ala
                245                 250                 255

Gly Leu Pro Ala Gln Val Met Ile Asp Phe Ser His Ala Asn Ser Ser
                260                 265                 270

Lys Gln Phe Lys Lys Gln Met Asp Val Cys Ala Asp Val Cys Gln Gln
        275                 280                 285

Ile Ala Gly Gly Glu Lys Ala Ile Ile Gly Val Met Val Glu Ser His
        290                 295                 300

Leu Val Glu Gly Asn Gln Ser Leu Glu Ser Gly Glu Pro Leu Ala Tyr
305                 310                 315                 320

Gly Lys Ser Ile Thr Asp Ala Cys Ile Gly Trp Glu Asp Thr Asp Ala
                325                 330                 335

Leu Leu Arg Gln Leu Ala Asn Ala Val Lys Ala Arg Arg Gly
                340                 345                 350

<210> SEQ ID NO 8
<211> LENGTH: 373
<212> TYPE: PRT
<213> ORGANISM: Escherichia coli

<400> SEQUENCE: 8

Met Val Ala Glu Leu Thr Ala Leu Arg Asp Gln Ile Asp Glu Val Asp
1               5                   10                  15

Lys Ala Leu Leu Asn Leu Leu Ala Lys Arg Leu Glu Leu Val Ala Glu
                20                  25                  30

Val Gly Glu Val Lys Ser Arg Phe Gly Leu Pro Ile Tyr Val Pro Glu
            35                  40                  45

Arg Glu Ala Ser Met Leu Ala Ser Arg Arg Ala Glu Ala Glu Ala Leu
        50                  55                  60

Gly Val Pro Pro Asp Leu Ile Glu Asp Val Leu Arg Arg Val Met Arg
65                  70                  75                  80

Glu Ser Tyr Ser Ser Glu Asn Asp Lys Gly Phe Lys Thr Leu Cys Pro
                85                  90                  95

Ser Leu Arg Pro Val Val Ile Val Gly Gly Gly Gln Met Gly Arg
                100                 105                 110
```

-continued

```
Leu Phe Glu Lys Met Leu Thr Leu Ser Gly Tyr Gln Val Arg Ile Leu
        115                 120                 125

Glu Gln His Asp Trp Asp Arg Ala Ala Asp Ile Val Ala Asp Ala Gly
        130                 135                 140

Met Val Ile Val Ser Val Pro Ile His Val Thr Glu Gln Val Ile Gly
145                 150                 155                 160

Lys Leu Pro Pro Leu Pro Lys Asp Cys Ile Leu Val Asp Leu Ala Ser
                165                 170                 175

Val Lys Asn Gly Pro Leu Gln Ala Met Leu Val Ala His Asp Gly Pro
            180                 185                 190

Val Leu Gly Leu His Pro Met Phe Gly Pro Asp Ser Gly Ser Leu Ala
        195                 200                 205

Lys Gln Val Val Val Trp Cys Asp Gly Arg Lys Pro Glu Ala Tyr Gln
        210                 215                 220

Trp Phe Leu Glu Gln Ile Gln Val Trp Gly Ala Arg Leu His Arg Ile
225                 230                 235                 240

Ser Ala Val Glu His Asp Gln Asn Met Ala Phe Ile Gln Ala Leu Arg
                245                 250                 255

His Phe Ala Thr Phe Ala Tyr Gly Leu His Leu Ala Glu Glu Asn Val
                260                 265                 270

Gln Leu Glu Gln Leu Leu Ala Leu Ser Ser Pro Ile Tyr Arg Leu Glu
        275                 280                 285

Leu Ala Met Val Gly Arg Leu Phe Ala Gln Asp Pro Gln Leu Tyr Ala
        290                 295                 300

Asp Ile Ile Met Ser Ser Glu Arg Asn Leu Ala Leu Ile Lys Arg Tyr
305                 310                 315                 320

Tyr Lys Arg Phe Gly Glu Ala Ile Glu Leu Leu Glu Gln Gly Asp Lys
                325                 330                 335

Gln Ala Phe Ile Asp Ser Phe Arg Lys Val Glu His Trp Phe Gly Asp
                340                 345                 350

Tyr Ala Gln Arg Phe Gln Ser Glu Ser Arg Val Leu Leu Arg Gln Ala
            355                 360                 365

Asn Asp Asn Arg Gln
        370
```

HOST CELLS AND METHODS FOR PRODUCING HYDROXYTYROSOL

RELATED PATENT APPLICATIONS

This application is a continuation of international Application No. PCT/US2017/039329, filed Jun. 26, 2017, which claims the benefit of U.S. Provisional Patent Application Ser. No. 62/354,657, filed Jun. 24, 2016, which applications are herein incorporated by reference in their entirety.

STATEMENT OF GOVERNMENTAL SUPPORT

The invention described and claimed herein was made utilizing funds supplied by the U.S. Department of Energy under Contract No. DE-AC02-05CH11231. The government has certain rights in this invention.

REFERENCE TO A "SEQUENCE LISTING" SUBMITTED AS ASCII TEXT FILES VIA EFS-WEB

The Sequence Listing written in file 077429_1114441_Sequence_Listing.txt created on Mar. 11, 2019, 25,228 bytes, machine format IBM-PC, MS-Windows operating system, in accordance with 37 C.F.R. §§ 1.821- to 1.825, is hereby incorporated by reference in its entirety for all purposes.

FIELD OF THE INVENTION

The present invention is in the field of production of hydroxytyrosol.

BACKGROUND OF THE INVENTION

Hydroxylation of aromatic rings is an important reaction used for the preparation of many valuable compounds including L-3,4-dihydroxyphenylalanine (L-DOPA) for the treatment of Parkinson's disease, benzylisoquinoline alkaloids, and melatonin. Compared with chemical reaction which frequently uses metallic oxidants in organic solvent, hydroxylation of aromatic ring by microorganisms is an interesting and promising method to synthesize the desired products in a single-step with a high regioselectivity and under mild conditions. Microbial aromatic hydroxylation is involved in the aerobic metabolism of aromatic compounds and mostly performed by oxygenases and tyrosinases during the degradation process either to relieve the toxicity or to metabolize them into organic acid to use as carbon sources.

Tyrosinase is an oxidoreductase belongs to type-3 copper protein which includes hemocyanins as an oxygen carrier. (Olivares, 2009; Robb, 1984) This enzyme involves multiple oxidation reaction of L-tyrosine using molecular oxygen as oxidant; the first oxidation step is o-hydroxylation of L-tyrosine to L-DOPA and is known to be the slowest step, and the second oxidation step is the production of o-quinone from o-diphenol which is fast and followed by non-enzymatic reaction to dopachrome, a colored intermediate to melanin pathway. Microbial conversion of tyrosine to L-DOPA is slow process, and the over-oxidation to ortho-quinone is hard to avoid when tyrosinase is used. The use of reducing agent such as ascorbic acid adds more step for the purification of the product from fermentation broth.

L-DOPA is an important compound to living cells, especially in animal since it is used as a precursor for many neurotransmitters, and in animal brain, L-DOPA was synthesized by tyrosine hydroxylase (TH) with tetrahydrobiopterin (BH4) as a cofactor. (Kappock, Chem. Rev. 1996; Fitzpatrick, Ann Rev Biochem 1999; Daubner, Arch Biochem Biophys 2011) The use of pterin cofactor during the oxidation step is unique feature of TH and related enzyme such as phenylalanine hydroxylase (PAH) and tryptophan hydroxylase (TPH), (Pribat, J. Bacteriol. 2010) and this helps to prevent over-oxidation of L-tyrosine to o-quinone product which is a problem in microbial L-DOPA production by tyrosinase (Maass, 2003). However, the application of TH enzyme to microbial metabolic engineering has not been reported due to the unavailability of the coenzyme BH4 in microbes. BH4 is a unique co-factor found in animal and no bacterial system has been reported to use BH4 for biosynthesis of L-DOPA or related metabolites.

Hydroxytyrosol (HTy) is a high value compound and there is an increasing demand for the stable and sustainable production of HTy with high purity. HTy is one of the most powerful antioxidants with potential biological function as an anti-tumor, anti-atheragenic, anti-inflammatory and/or anti-platelet aggregation agent. It has a wide range of potential applications in industry, such as functional food, dietary supplement, cosmetics, and animal feed.

Currently HTy is produced from enriched olive extracts after chemical or enzymatic hydrolysis. However, this method is difficult to apply for a high purity product, since the extracts are complex mixtures of compounds with similar structures.

SUMMARY OF THE INVENTION

The present invention provides for a composition comprising: (a) a first host cell capable of producing L-DOPA; and (b) a second host cell capable of converting L-DOPA into hydroxytyrosol (HTy); wherein any one or both of the first host cell and the second host cell is a genetically modified host cell. In some embodiments, the first host cell is a first genetically modified host cell, and the second host cell is a second genetically modified host cell.

In some embodiments, the first host cell comprises dihydropteridine reductase (DHPR), pterin-4-alpha-carbinolamine dehydratase (PCD), and tyrosine hydroxylase (TH), or any homologous enzyme thereof. In some embodiments, one or more of DHPR, PCD, and TH are heterologous to the first host cell.

In some embodiments, the first host cell is engineered to overproduce tyrosine compared to a non-engineered cell, and the first host cell comprises tyrosine hydroxylase (TH), or a homologous enzyme thereof. In some embodiments, the first host cell is a feedback resistant mutant comprising a means to overexpress AroG, or any homologous enzymes thereof, and a means to overexpress TyrA, or a homologous enzyme thereof. In some embodiments, the means to overexpress AroG is one or more copies of the aroG gene introduced into the host cell, either integrated in a chornosome of the host cell or on a plasmid. In some embodiments, the means to overexpress TyrA is one or more copies of the tyrA gene introduced into the host cell, either integrated in a chornosome of the host cell or on a plasmid. In some embodiments, the aroG and/or tyrA genes are transcribed from a strong constitutive promoter. In some embodiments, the first host cell comprises one or more, or all, of the following enzymes, or a corresponding homologous enzyme thereof, for the synthesis of L-tyrosine: phosphoenolpyruvate synthase (PpsA), transketolase A (TktA), DAHP synthase (AroG), DHQ synthase (AroB), DHQ dehydratase (AroD), quinate/shikimate dehydrogenase (YdiB), shikimate dehydrogenase (AroE), shikimate kinase I/II (AroK/L), EPSP synthase (AroA), chorismate synthase (AroC), chorismate mutase/prephenate dehydrogenase (TyrA), and tyrosine aminotransferase (TyrB). In some embodiments, the first host cell is engineered to overproduce tyrosine is capable of producing 2.0, 2.1, 2.2, 2.3, 2.4, 2.5, or 2.6, or more, mM of L-tyrosine when the first host cell is grown or cultured in a M9Y defined medium (1% glucose).

In some embodiments, the second host cell comprises L-DOPA decarboxylase (DDC), tyramine oxidase (TYO), and alcohol dehydrogenase (ADH), or any homologous enzyme thereof. In some embodiments, one or more of DDC, TYO, and ADH are heterologous to the second host cell.

The present invention provides for a method for producing HTy comprising: (a) providing a first host cell, (b) culturing the first host cell to produce a first culture, (c) providing a second host cell, (d) optionally culturing the second host cell to produce a second culture, (e) combining or mixing the first and second cultures to produce a co-culture comprising the composition of the present invention, and (f) culturing the first and second host cells in the composition such that HTy is produced, and (g) optionally extracting or separating the HTy from the co-culture.

The present invention provides for a production method to produce HTy with significant improvement in titer from what was previously reported (Satoh et al. Metabolic Engineering 14 (2012) 603-610). In some embodiments, there are four metabolic and process engineering approaches to improve the efficiency of the synthetic HTy pathway (FIG. 1).

The HTy pathway comprises five heterologous enzymes (i.e., heterologous to each other) for tyrosine hydroxylation and downstream conversion of L-DOPA to HTy (FIG. 2).

The present invention also provides for a bioreactor design for industrial application comprising the composition of the present invention.

The present invention also provides for a genetically modified host cell useful for the methods of the present invention.

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION OF THE INVENTION

Figure 1:
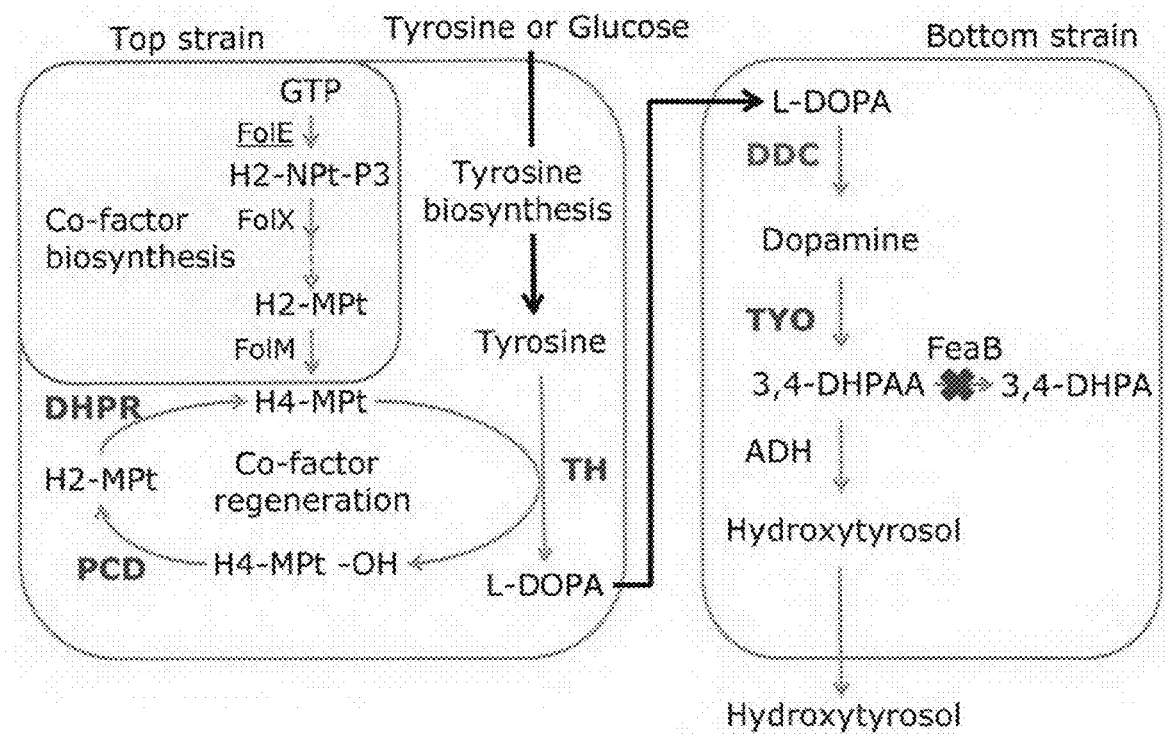
FIG. 1. Summary of hydroxytyrosol producer engineering.
Figure 2:
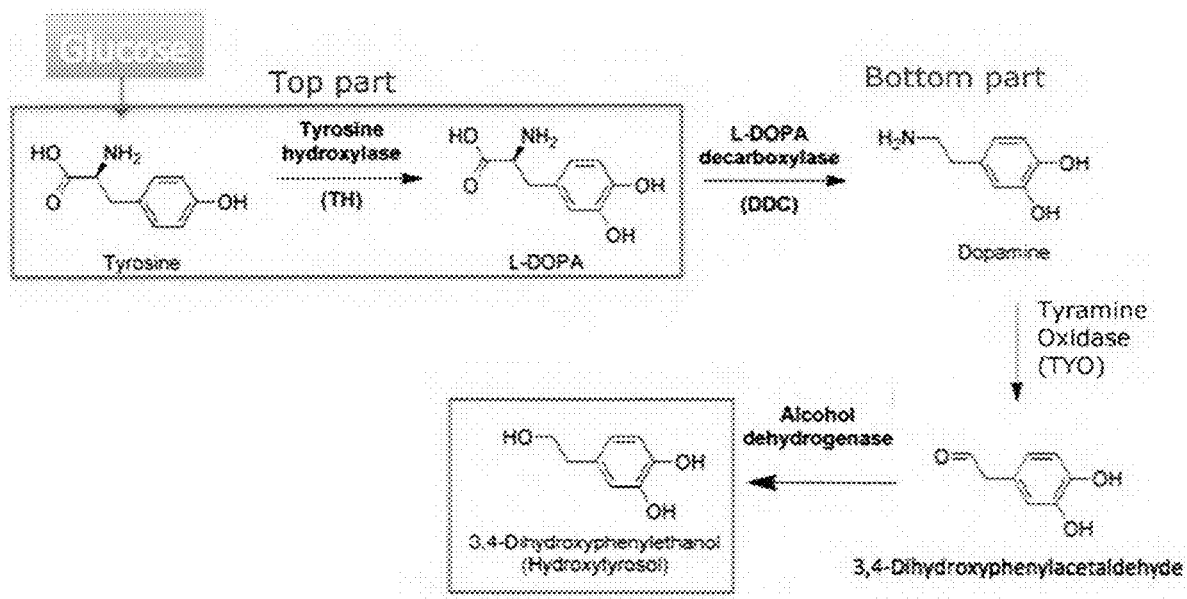
FIG. 2. Hydroxytyrosol production pathway. TH: tyrosine hydroxylase from mouse, synthesized. DDC: L-DOPA decarboxylase from pig, synthesized. MAO: monoamine oxidase from *Micrococcus luteus,* cloned.

Before the invention is described in detail, it is to be understood that, unless otherwise indicated, this invention is not limited to particular sequences, expression vectors, enzymes, host microorganisms, or processes, as such may vary. It is also to be understood that the terminology used herein is for purposes of describing particular embodiments only, and is not intended to be limiting.

As used in the specification and the appended claims, the singular forms "a," "an," and "the" include plural referents unless the context clearly dictates otherwise. Thus, for example, reference to an "expression vector" includes a single expression vector as well as a plurality of expression vectors, either the same (e.g., the same operon) or different; reference to "cell" includes a single cell as well as a plurality of cells; and the like.

In this specification and in the claims that follow, reference will be made to a number of terms that shall be defined to have the following meanings:

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

The terms "host cell" and "host microorganism" are used interchangeably herein to refer to a living biological cell, such as a microbe, that can be transformed via insertion of an expression vector. Thus, a host organism or cell as described herein may be a prokaryotic organism (e.g., an organism of the kingdom Eubacteria) or a eukaryotic cell. As will be appreciated by one of ordinary skill in the art, a prokaryotic cell lacks a membrane-bound nucleus, while a eukaryotic cell has a membrane-bound nucleus.

The term "heterologous DNA" as used herein refers to a polymer of nucleic acids wherein at least one of the following is true: (a) the sequence of nucleic acids is foreign to (i.e., not naturally found in) a given host microorganism; (b) the sequence may be naturally found in a given host microorganism, but in an unnatural (e.g., greater than expected) amount; or (c) the sequence of nucleic acids comprises two or more subsequences that are not found in the same relationship to each other in nature. For example, regarding instance (c), a heterologous nucleic acid sequence that is recombinantly produced will have two or more sequences from unrelated genes arranged to make a new functional nucleic acid. Specifically, the present invention describes the introduction of an expression vector into a host microorganism, wherein the expression vector contains a nucleic acid sequence coding for an enzyme that is not normally found in a host microorganism. With reference to the host microorganism's genome, then, the nucleic acid sequence that codes for the enzyme is heterologous.

The terms "expression vector" or "vector" refer to a compound and/or composition that transduces, transforms, or infects a host microorganism, thereby causing the cell to express nucleic acids and/or proteins other than those native to the cell, or in a manner not native to the cell. An "expression vector" contains a sequence of nucleic acids (ordinarily RNA or DNA) to be expressed by the host microorganism. Optionally, the expression vector also comprises materials to aid in achieving entry of the nucleic acid into the host microorganism, such as a virus, liposome, protein coating, or the like. The expression vectors contemplated for use in the present invention include those into which a nucleic acid sequence can be inserted, along with any preferred or required operational elements. Further, the expression vector must be one that can be transferred into a host microorganism and replicated therein. Preferred expression vectors are plasmids, particularly those with restriction sites that have been well documented and that contain the operational elements preferred or required for transcription of the nucleic acid sequence. Such plasmids, as well as other expression vectors, are well known to those of ordinary skill in the art.

The term "transduce" as used herein refers to the transfer of a sequence of nucleic acids into a host microorganism or cell. Only when the sequence of nucleic acids becomes stably replicated by the cell does the host microorganism or cell become "transformed." As will be appreciated by those of ordinary skill in the art, "transformation" may take place either by incorporation of the sequence of nucleic acids into the cellular genome, i.e., chromosomal integration, or by extrachromosomal integration. In contrast, an expression vector, e.g., a virus, is "infective" when it transduces a host microorganism, replicates, and (without the benefit of any complementary virus or vector) spreads progeny expression vectors, e.g., viruses, of the same type as the original transducing expression vector to other microorganisms, wherein the progeny expression vectors possess the same ability to reproduce.

As used herein, the terms "nucleic acid sequence," "sequence of nucleic acids," and variations thereof shall be generic to polydeoxyribonucleotides (containing 2-deoxy-D-ribose), to polyribonucleotides (containing D-ribose), to any other type of polynucleotide that is an N-glycoside of a purine or pyrimidine base, and to other polymers containing nonnucleotidic backbones, provided that the polymers contain nucleobases in a configuration that allows for base pairing and base stacking, as found in DNA and RNA. Thus, these terms include known types of nucleic acid sequence modifications, for example, substitution of one or more of the naturally occurring nucleotides with an analog; intemucleotide modifications, such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., arninoalklyphosphoramidates, aminoalkylphosphotriesters); those containing pendant moieties, such as, for example, proteins (including nucleases, toxins, antibodies, signal peptides, poly-L-lysine, etc.); those with intercalators (e.g., acridine, psoralen, etc.); and those containing chelators (e.g., metals, radioactive metals, boron, oxidative metals, etc.). As used herein, the symbols for nucleotides and polynucleotides are those recommended by the IUPAC-IUB Commission of Biochemical Nomenclature (*Biochem.* 9:4022, 1970).

The term "operably linked" refers to a functional linkage between a nucleic acid expression control sequence (such as a promoter) and a second nucleic acid sequence, wherein the expression control sequence directs transcription of the nucleic acid corresponding to the second sequence.

In some embodiments, the method comprises culturing the genetically modified host cell with exogenously provided tyrosine, or a suitable carbon source. When the method comprises culturing the genetically modified host cell with a suitable carbon source, the genetically modified host cell is capable of synthesizing tyrosine using a native biosynthetic pathway or a heterologous biosynthetic pathway residing on one or more nucleic acids in the host cell, wherein the one or more nucleic acids are on one or more vectors or stably integrated into a host cell chromosome. Suitable carbon sources which the host cell is capable of uptaking and metabolizing. Such carbon sources include but are not limited to sugars, such as monosaccharides, such as glucose.

In some embodiments, the method comprises: (a) introducing a nucleic acid construct encoding an enzyme capable of catalyzing the oxidation of the aromatic amino acid into a genetically modified host cell; and (b) culturing the genetically modified host cell under a suitable condition such that the enzyme is expressed in the host cell; such that the culturing results in the genetically modified host cell producing the desired products.

In some embodiments, the one or more enzymes are capable of catalyzing the oxidation of tyrosine into L-DOPA, dopamine, 3,4-dihydroxyphenylacetaldehyde, 3,4-dihydroxypehylethanol (hydroxytyrosol), reticuline, thebaine, and/or morphine, such that the culturing the host cell results in the host cell producing L-DOPA, dopamine, 3,4-dihydroxyphenylacetaldehyde, 3,4-dihydroxypehyletha- nol (hydroxytyrosol), reticuline, thebaine, and/or morphine.

In some embodiments, the host cell is capable of endog- enously producing tyrosine, either by native enzymes of the tyrosine biosynthetic pathway, or a heterologous tyrosine biosynthetic pathway introduced into the host cell. In some embodiments, the tyrosine biosynthetic pathway comprises one or more of the following enzymes, or any corresponding homologous enzymes thereof: PpsA, TktA, AroG, AroB, AroD, YdiB, AroE, AroK/L, AroA, AroC, TyrA, and TyrB. In some embodiments, the host cell over produces AroB and/or TyrA, or any corresponding homologous enzymes thereof.

In some embodiments, the host cell comprises or is capable of expressing TH, DDC, MAO, and/or alcohol dehydrogenase, or homologous enzymes thereof, wherein one or more of the enzymes are overproduced compared to the unmodified host cell or one or more of the enzymes is heterologous to the host cell. In some embodiments, the host cell is capable of endogenously producing tyrosine, either by native enzymes of the tyrosine biosynthetic pathway, or a heterologous tyrosine biosynthetic pathway introduced into the host cell.

In some embodiments, the host cell comprises or is capable of expressing heterologous TH (such as mouse TH), heterologous DDC (such as pig DDC), and/or heterologous MAO (such as *M. luteus* MAO), or homologous enzymes thereof.

In some embodiments, the host cell natively comprises a nucleic acid encoding an enzyme capable of catalyzing phenylacetaldehyde dehydrogenase into 3,4-dihydroxyphe- nyl acetate (3,4-DHPA), such as the enzyme phenylacetal- dehyde dehydrogenase, wherein the host cell is reduced in the expression of the enzyme. When the host cell is *E. coli*, the enzyme is phenylacetaldehyde dehydrogenase encoded by the feaB gene. The reduced expression can be the result of a mutation that reduced expression or reduces enzymatic activity of the enzyme. An example of such a mutation is a truncated or deleted gene, such as a knock out mutation.

One means to have a host cell synthesize MH4 is to have the host cell comprise the enzymes GTP cyclohydrolase I (folE), folX, P-ase, and folM, or homologous enzymes thereof.

Tyrosine hydroxylase is an enzyme that uses tetrahydro- biopterin (BH4) or MH4 in the catalysis of tyrosine and tryptophan into L-DOPA and 5-hydroxy-tryptophan, respec- tively. Pterin-4-alpha-carbinolamine dehydratase (PCD) and dihydropteridine reductase (DHPR) are capable of catalyz- ing the reactions for BH4 regeneration. In some embodi- ments, when the genetically modified host cell comprises tyrosine hydroxylase (TH), the host cell further comprises pterin-4-alpha-carbinolamine dehydratase (PCD), or a homologous enzyme thereof, and dihydropteridine reductase (DHPR), or a homologous enzyme thereof. In some embodiments, when the genetically modified host cell does not naturally synthesize BH4, the host cell further comprises GTP cyclohydrolase I (folE), 6-pyruvoyl-tetrahy- dropterin synthase (PTPS), and sepiapterin reductase (SR), or one or more homologous enzymes thereof.

In some embodiments of invention, the method further comprises the step of recovering the produced one or more oxidation products, wherein the recovering step is concur- rent or subsequent to the culturing step.

Enzymes, and Nucleic Acids Encoding Thereof

A homologous enzyme is an enzyme that has a polypep- tide sequence that is at least 70%, 75%, 80%, 85%, 90%, 95% or 99% identical to any one of the enzymes described in this specification or in an incorporated reference. The homologous enzyme retains amino acids residues that are recognized as conserved for the enzyme. The homologous enzyme may have non-conserved amino acid residues replaced or found to be of a different amino acid, or amino acid(s) inserted or deleted, but which does not affect or has insignificant effect on the enzymatic activity of the homolo- gous enzyme. The homologous enzyme has an enzymatic activity that is identical or essentially identical to the enzy- matic activity any one of the enzymes described in this specification or in an incorporated reference. The homolo- gous enzyme may be found in nature or be an engineered mutant thereof.

A suitable tyrosine hydroxylase or tyrosine 3-monooxy- genase is mouse tyrosine hydroxylase (NP_033403), or a homologous enzyme thereof, which has the following amino acid sequence:

```
                                                          (SEQ ID NO: 1)
  1 mptpsasspq pkgfrrayse qdtkqaeavt sprfigrrqs liedarkere aaaaaaaaav 61 asaepgnple avvfeerdgn avlnllfslr gtkpsslsra lkvfetfeak ihhletrpaq 121 rplagsphle yfvrfevpsg dlaallssyr rvsddyrsar edkvpwfprk vseldkchhl 181 vtkfdpdldl dhpgfsdqay rqrrkliaei afqykqgepi phveytkeei atwkevyatl 241 kglyathacr ehleafqlle rycgyredsi pqledvshfl kertgfqlrp vagllsardf 301 laslafrvfq ctqyirhass pmhspepdcc hellghvpml adrtfaqfsq diglaslgas 361 deeieklstv ywftvefglc kqngelkayg agllssygel lhslseepev rafdpdtaav 421 qpyqdqtyqp vyfvsesfsd akdklrnyas riqrpfsvkf dpytlaidvl dsphtirrsl 481 egvqdelhtl tqalsais
```

A suitable pterin-4-alpha-carbinolamine dehydratase (PCD) is human PCD (NP_000272), or a homologous enzyme thereof, which has the following amino acid sequence:

```
                                                          (SEQ ID NO: 2)
  1 magkahrlsa eerdqllpnl ravgwneleg rdaifkqfhf kdfnrafgfm trvalqaekl 61 dhhpewfnvy nkvhitlsth ecaglserdi nlasfieqva vsmt
```

A suitable dihydropteridine reductase (DHPR) is human DHPR (P09417), or a homologous enzyme thereof, which has the following amino acid sequence:

```
                                                          (SEQ ID NO: 3)
  1 maaaaaagea rrvlvyggrg algsrcvgaf rarnwwvasv dvveneeasa siivkmtdsf 61 teqadqvtae vgkllgeekv dailcvaggw aggnaksksl fkncdlmwkg siwtstissh 121 latkhlkegg lltlagakaa ldgtpgmigy gmakgavhql cqslagknsg mppgaaaiav 181 lpvtldtpmn rksmpeadfs swtpleflve tfhdwitgkn rpssgsliqv vttegrtelt 241 payf
```

A suitable L-DOPA decarboxylase (DDC) is pig DDC, or a homologous enzyme thereof, which has the following nucleotide (SEQ ID NO:4) and amino acid (SEQ ID NO:5) sequences:

```
-10                           GAATTCACATATGAATGCCAGCGATTTC
                                       M  N  A  S  D  F        6

19 CGTCGACGCGGCAAAGAAATGGTGGATTACATGGCGGATTACCTGGAAGGCATCGAAGGT
     R  R  R  G  K  E  M  V  D  Y  M  A  D  Y  L  E  G  I  E  G    26

79 CGTCAGGTGTACCCGGATGTGCAGCCGGGGTACCTGCGTCCGCTGATCCCGGCGACCGCC
     R  Q  V  Y  P  D  V  Q  P  G  Y  L  R  P  L  I  P  A  T  A    46

139 CCGCAGGAACCGGATACCTTCGAAGATATCCTGCAGGATGTGGAAAAAATCATCATGCCG
     P  Q  R  P  D  T  F  E  D  I  L  Q  D  V  E  K  I  I  M  P    66

199 GGGGTGACCCACTGGCACAGCCCGTACTTCTTCGCGTACTTCCCGACCGCCAGCAGCTAC
     G  V  T  H  W  H  S  P  Y  F  F  A  Y  A  P  T  A  S  S  Y    86

259 CCGGCGATGCTGGCGGATATGCTGTGCGGTGCGATCGGATGCATCGGTTTCAGCTGGGCG
     P  A  M  L  A  D  M  L  C  G  A  I  G  C  I  G  F  S  W  A   106

319 GCTAGCCCGGCGTGCACCGAACTCGAGACCGTGATGATGGATTGGCTGGGCAAAATGCTC
     A  S  P  A  C  T  E  L  E  T  V  M  M  D  W  L  G  K  M  L   126

379 CAGCTTCCGGAAGCGTTCCTGGCGGGCGAAGCCGGTGAAGGCGGCGGCGTGATCCAGGGT
     Q  L  P  E  A  F  L  A  G  E  A  G  E  G  G  G  V  I  Q  G   146

439 AGCGCCAGCGAAGCCACCCTGGTGGCGCTGCTGGCGGCGCGTACCAAAGTGGTGCGACGT
     S  A  S  E  A  T  L  V  A  L  L  A  A  R  T  K  V  V  R  R   166

499 CTGCAAGCGGCGAGCCCGGGCCTGACCCAGGGCGCGGTGCTGGAAAAACTAGTGGCGTAC
     L  Q  A  A  S  P  G  L  T  Q  G  A  V  L  E  K  L  V  A  Y   186

559 GCGAGTGATCAGGCGCACAGCAGCGTGGAACGTGCCGGCCTGATCGGCGGCGTGAAACTG
     A  S  D  Q  A  H  S  S  V  E  R  A  G  L  I  G  G  V  K  L   206

619 AAAGCGATCCCGAGCGATGGCAAATTCGCGATGCGTGCGAGCGCGCTGCAGGAGGCCCTG
     K  A  I  P  S  D  G  K  F  A  M  R  A  S  A  L  Q  E  A  L   226

679 GAGAGAGACAAGGCTGCCGGCCTGATTCCTTTCTTCGTGGTGGCTACGCTGGGGACCACA
     E  R  D  K  A  A  G  L  I  P  F  F  V  V  A  T  L  G  T  T   246

739 TCGTGCTGCTCCTTTGACAATCTCTTAGAAGTGGGACCCATCTGTCACGAAGAGGACATA
     S  C  C  S  F  D  N  L  L  E  V  G  P  I  C  H  E  E  D  I   266

799 TGGCTGCACGTGGATGCTGCCTACGCAGGCAGTGCCTTCATCTGCCCTGAGTTCCGGCAC
     W  L  H  V  D  A  A  Y  A  H  S  A  F  I  C  P  E  F  R  H   286

859 CTGCTGAATGGAGTGGAGTTTGCAGATTCATTTAACTTTAATCCCCACAAATGGCTCTTG
     L  L  N  G  V  E  F  A  D  S  F  N  F  N  P  H  K  W  L  L   306

919 GTGAATTTTGACTGCTCGGCTATGTGGGTGAAAAGGAGAACGGACCTGACTGGAGCCTTC
     V  N  F  D  C  S  A  M  W  V  K  R  R  T  D  L  T  G  A  F   326
```

```
                                                                -continued
 979 AAATTGGACCCCGTGTACTTAAAGCACAGCCACCAGGGCTCGGGGCTTATCACGGACTAC
       K   L   D   P   V   Y   L   K   H   S   H   Q   G   S   G   L   I   T   D   Y     346

1039 AGGCACTGGCAGCTGCCACTGGGTCGGCGATTCCGGTCCCTGAAAATGTGGTTTGTTTTT
       R   H   W   Q   L   P   L   G   R   R   F   R   S   L   K   M   W   F   V   F     366

1099 AGGATGTACGGAGTCAAGGGACTGCAGGCCTATATCCGCAAGCACGTGCAGCTGTCTCAT
       R   M   Y   G   V   K   G   L   Q   A   Y   I   R   K   H   V   Q   L   S   H     386

1159 GAGTTTGAGGCATTTGTGCTTCAGGATCCACGCTTTGAAGTCTGTGCCGAAGTCACCCTG
       E   F   E   A   F   V   L   Q   D   P   R   F   E   V   C   A   E   V   T   L     406

1219 GGGCTGGTGTGTTTCCGGCTGAAGGGCTCCGACGGACTGAATGAAGCGCTTCTGGAAAGG
       G   L   V   C   F   R   L   K   G   S   D   G   L   N   E   A   L   L   E   R     426

1279 ATAAACAGCGCCAGGAAAATCCACTTGGTTCCCTGTCGCCTGAGGGGCCAGTTCGTGCTG
       I   N   S   A   R   K   I   H   L   V   P   C   R   L   R   G   Q   F   V   L     446

1339 CGGTTCGCCATCTGCTCGCGCAAGGTGGAGTCGGGCCACGTGCGGCTGGCCTGGGAGCAC
       R   F   A   I   C   S   R   K   V   E   S   G   H   V   R   L   A   W   E   H     466

1399 ATCCGAGGGCTGGCGGCCGAGCTGCTGGCCGCGGAGGAGGGAAAGGCAGAGATCAAAAGT
       I   R   G   L   A   A   E   L   L   A   A   E   E   G   K   A   E   I   K   S     486

1459 TGAAGTGCCCTGAAGAGCAGAATCGGAGGAGACGCGTCGTCCCCGCTCCGAGGCGTAGAG
       *

1519 CCTGCAATGGTCCCCCAGTTCTTTAGCCCACGTTCTCCAGAAAGAAGCTTGTGCCTACG

1579 TCTGACCAGCCTCTCAGCAATGAAGAAGTATTATTTGCTCTTTGAAAAGTTAATCCCAGT

1639 GGAGACAGCTTTTACTCTTTATTTGGCTGTGATTGTTTGTTGATTAAAACATCATAGGTT

1699 TCTGCATCCTTGAAGTTGTCAGCGGTGGTCCACTTTCCGGGGCAACCTATGCTGATGGGA

1759 TTTGAGATGATACCCGTGGTCTTTAAATTACTCTGTCCTGTGGCTTATGCTTAATAAATG

1819 ATGTGAAGTGTAAAAAAAAAAAAAAAAAAAA
```

A suitable monoamine oxidase (MAO) is Micrococcus luteus MAO (ACS30544.1), or a homologous enzyme thereof, which has the following amino acid sequence:

(SEQ ID NO: 6)
```
  1 mttapatagr errtsdvvvi gagpaglmaa rtakagglsv tvlearrrvg grtwnglveg
 61 adgkdhfiei ggqwispdqt rlislveelg lptfsrfrdg rnvyvdprge rhvydgldfp
121 vaektdremd rliakidelt aeidaaapwe hpraaeldti sfrhwleqes ddpeaidnvs
181 iyiasgmltk pshtfsmlqa llmaasagsf rnlvdedfil dkrveggmqs vsltmaaelg
241 ddvvlgqpvr tlrwaepdps tadekngvaa dvrngvandg aagdvvaltd dyevharyav
301 lavppnlysr isfeppmpre ggiahqhism glvikvhavy etpfwreegl sgtcfgggrl
361 vqeiydntnr genlaggapg eedphgtivg fvsdvyaeqm walpeeerka ailgamaeyl
421 gprtlepiaf flsdmaaeew trgayatsyd lgglsrwghl qnrptgpihy acsdiaaegy
481 qhvdgairmg eaaalaiaer eatdagqptg
```

A suitable AroG is E. coli AroG, or a homologous enzyme thereof, which has the following amino acid sequence:

(SEQ ID NO: 7)
```
MNYQNDDLRI KEIKELLPPV ALLEKFPATE NAANTVAHAR
KAIHKILKGN DDRLLVVIGP CSIHDPVAAK EYATRLLALR
EELKDELEIV MRVYFEKPRT TVGWKGLIND PHMDNSFQIN
DGLRIARKLL LDINDSGLPA AGEFLDMITP QYLADLMSWG
AIGARTTESQ VHRELASGLS CPVGFKNGTD GTIKVAIDAI
NAAGAPHCFL SVTKWGHSAI VNTSGNGDCH IILRGGKEPN
YSAKHVAEVK EGLNKAGLPA QVMIDFSHAN SSKQFKKQMD
VCADVCQQIA GGEKAIIGVM VESHLVEGNQ SLESGEPLAY
GKSITDACIG WEDTDALLRQ LANAVKARRG
```

A suitable TyrA is E. coli TyrA, or a homologous enzyme thereof, which has the following amino acid sequence:

```
                                         (SEQ ID NO: 8)
MVAELTALRD  QIDEVDKALL  NLLAKRLELV  AEVGEVKSRF

GLPIYVPERE  ASMLASRRAE  AEALGVPPDL  IEDVLRRVMR

ESYSSENDKG  FKTLCPSLRP  VVIVGGGGQM  GRLFEKMLTL

SGYQVRILEQ  HDWDRAADIV  ADAGMVIVSV  PIHVTEQVIG

KLPPLPKDCI  LVDLASVKNG  PLQAMLVAHD  GPVLGLHPMF

GPDSGSLAKQ  VVVWCDGRKP  EAYQWFLEQI  QVWGARLHRI

SAVEHDQNMA  FIQALRHFAT  FAYGLHLAEE  NVQLEQLLAL

SSPIYRLELA  MVGRLFAQDP  QLYADIIMSS  ERNLALIKRY

YKRFGEAIEL  LEQGDKQAFI  DSFRKVEHWF  GDYAQRFQSE

SRVLLRQAND  NRQ
```

The nucleic acid constructs of the present invention comprise nucleic acid sequences encoding one or more of the subject enzymes. The nucleic acid of the subject enzymes are operably linked to promoters and optionally control sequences such that the subject enzymes are expressed in a host cell cultured under suitable conditions. The promoters and control sequences are specific for each host cell species. In some embodiments, expression vectors comprise the nucleic acid constructs. Methods for designing and making nucleic acid constructs and expression vectors are well known to those skilled in the art.

Sequences of nucleic acids encoding the subject enzymes are prepared by any suitable method known to those of ordinary skill in the art, including, for example, direct chemical synthesis or cloning. For direct chemical synthesis, formation of a polymer of nucleic acids typically involves sequential addition of 3'-blocked and 5'-blocked nucleotide monomers to the terminal 5'-hydroxyl group of a growing nucleotide chain, wherein each addition is effected by nucleophilic attack of the terminal 5'-hydroxyl group of the growing chain on the 3'-position of the added monomer, which is typically a phosphorus derivative, such as a phosphotriester, phosphoramidite, or the like. Such methodology is known to those of ordinary skill in the art and is described in the pertinent texts and literature (e.g., in Matteuci et al. (1980) *Tet. Lett.* 521:719; U.S. Pat. Nos. 4,500,707; 5,436,327; and 5,700,637). In addition, the desired sequences may be isolated from natural sources by splitting DNA using appropriate restriction enzymes, separating the fragments using gel electrophoresis, and thereafter, recovering the desired nucleic acid sequence from the gel via techniques known to those of ordinary skill in the art, such as utilization of polymerase chain reactions (PCR; e.g., U.S. Pat. No. 4,683,195).

Each nucleic acid sequence encoding the desired subject enzyme can be incorporated into an expression vector. Incorporation of the individual nucleic acid sequences may be accomplished through known methods that include, for example, the use of restriction enzymes (such as BamHI, EcoRI, HhaI, XhoI, XmaI, and so forth) to cleave specific sites in the expression vector, e.g., plasmid. The restriction enzyme produces single stranded ends that may be annealed to a nucleic acid sequence having, or synthesized to have, a terminus with a sequence complementary to the ends of the cleaved expression vector. Annealing is performed using an appropriate enzyme, e.g., DNA ligase. As will be appreciated by those of ordinary skill in the art, both the expression vector and the desired nucleic acid sequence are often cleaved with the same restriction enzyme, thereby assuring that the ends of the expression vector and the ends of the nucleic acid sequence are complementary to each other. In addition, DNA linkers may be used to facilitate linking of nucleic acids sequences into an expression vector.

A series of individual nucleic acid sequences can also be combined by utilizing methods that are known to those having ordinary skill in the art (e.g., U.S. Pat. No. 4,683,195).

For example, each of the desired nucleic acid sequences can be initially generated in a separate PCR. Thereafter, specific primers are designed such that the ends of the PCR products contain complementary sequences. When the PCR products are mixed, denatured, and reannealed, the strands having the matching sequences at their 3' ends overlap and can act as primers for each other Extension of this overlap by DNA polymerase produces a molecule in which the original sequences are "spliced" together. In this way, a series of individual nucleic acid sequences may be "spliced" together and subsequently transduced into a host microorganism simultaneously. Thus, expression of each of the plurality of nucleic acid sequences is effected.

Individual nucleic acid sequences, or "spliced" nucleic acid sequences, are then incorporated into an expression vector. The invention is not limited with respect to the process by which the nucleic acid sequence is incorporated into the expression vector. Those of ordinary skill in the art are familiar with the necessary steps for incorporating a nucleic acid sequence into an expression vector. A typical expression vector contains the desired nucleic acid sequence preceded by one or more regulatory regions, along with a ribosome binding site, e.g., a nucleotide sequence that is 3-9 nucleotides in length and located 3-11 nucleotides upstream of the initiation codon in *E. coli*. See Shine et al. (1975) *Nature* 254:34 and Steitz, in Biological Regulation and Development: Gene Expression (ed. R. F. Goldberger), vol. 1, p. 349, 1979, Plenum Publishing, N.Y.

Regulatory regions include, for example, those regions that contain a promoter and an operator. A promoter is operably linked to the desired nucleic acid sequence, thereby initiating transcription of the nucleic acid sequence via an RNA polymerase enzyme. An operator is a sequence of nucleic acids adjacent to the promoter, which contains a protein-binding domain where a repressor protein can bind. In the absence of a repressor protein, transcription initiates through the promoter. When present, the repressor protein specific to the protein-binding domain of the operator binds to the operator, thereby inhibiting transcription. In this way, control of transcription is accomplished, based upon the particular regulatory regions used and the presence or absence of the corresponding repressor protein. An example includes lactose promoters (LacI repressor protein changes conformation when contacted with lactose, thereby preventing the LacI repressor protein from binding to the operator). Another example is the tac promoter. (See deBoer et al. (1983) *Proc. Natl. Acad. Sci. USA*, 80:21-25.) As will be appreciated by those of ordinary skill in the art, these and other expression vectors may be used in the present invention, and the invention is not limited in this respect.

Although any suitable expression vector may be used to incorporate the desired sequences, readily available expression vectors include, without limitation: plasmids, such as pSC101, pBR322, pBBR1MCS-3, pUR, pEX, pMR100, pCR4, pBAD24, pUC19; bacteriophages, such as M13 phage and λ phage. Of course, such expression vectors may only be suitable for particular host cells. One of ordinary skill in the art, however, can readily determine through routine experimentation whether any particular expression vector is suited for any given host cell. For example, the expression vector can be introduced into the host cell, which is then monitored for viability and expression of the sequences contained in the vector. In addition, reference may be made to the relevant texts and literature, which describe expression vectors and their suitability to any particular host cell.

The expression vectors of the invention must be introduced or transferred into the host cell. Such methods for transferring the expression vectors into host cells are well known to those of ordinary skill in the art. For example, one method for transforming *E. coli* with an expression vector involves a calcium chloride treatment wherein the expression vector is introduced via a calcium precipitate. Other salts, e.g., calcium phosphate, may also be used following a similar procedure. In addition, electroporation (i.e., the application of current to increase the permeability of cells to nucleic acid sequences) may be used to transfect the host microorganism. Also, microinjection of the nucleic acid sequencers) provides the ability to transfect host microorganisms. Other means, such as lipid complexes, liposomes, and dendrimers, may also be employed. Those of ordinary skill in the art can transfect a host cell with a desired sequence using these or other methods.

For identifying a transfected host cell, a variety of methods are available. For example, a culture of potentially transfected host cells may be separated, using a suitable dilution, into individual cells and thereafter individually grown and tested for expression of the desired nucleic acid sequence. In addition, when plasmids are used, an often-used practice involves the selection of cells based upon antimicrobial resistance that has been conferred by genes intentionally contained within the expression vector, such as the amp, gpt, neo, and hyg genes.

The host cell is transformed with at least one expression vector. When only a single expression vector is used (without the addition of an intermediate), the vector will contain all of the nucleic acid sequences necessary.

Once the host cell has been transformed with the expression vector, the host cell is allowed to grow. For microbial hosts, this process entails culturing the cells in a suitable medium. It is important that the culture medium contain an excess carbon source, such as a sugar (e.g., glucose) when an intermediate is not introduced. In this way, cellular production of aromatic amino acid ensured. When added, the intermediate is present in an excess amount in the culture medium.

As the host cell grows and/or multiplies, expression of the enzymes necessary for producing the oxidation product(s) is affected. Once expressed, the enzymes catalyze the steps necessary for carrying out the steps of optionally aromatic amino acid production, BH4 production, and oxidation product production. If an intermediate has been introduced, the expressed enzymes catalyze those steps necessary to convert the intermediate into the respective oxidation product. Any means for recovering the oxidation product from the host cell may be used. For example, the host cell may be harvested and subjected to hypotonic conditions, thereby lysing the cells. The lysate may then be centrifuged and the supernatant subjected to high performance liquid chromatography (HPLC) or gas chromatography (GC). Once the oxidation product is recovered, modification, as desired, may be carried out on the oxidation product.

Host Cells

The host cells of the present invention are genetically modified in that heterologous nucleic acid have been introduced into the host cells, and as such the genetically modified host cells do not occur in nature. The suitable host cell is one capable of expressing a nucleic acid construct encoding one or more enzymes described herein. The gene(s) encoding the enzyme(s) may be heterologous to the host cell or the gene may be native to the host cell but is operatively linked to a heterologous promoter and one or more control regions which result in a higher expression of the gene in the host cell.

The enzyme can be native or heterologous to the host cell. Where the enzyme is native to the host cell, the host cell is genetically modified to modulate expression of the enzyme. This modification can involve the modification of the chromosomal gene encoding the enzyme in the host cell or a nucleic acid construct encoding the gene of the enzyme is introduced into the host cell. One of the effects of the modification is the expression of the enzyme is modulated in the host cell, such as the increased expression of the enzyme in the host cell as compared to the expression of the enzyme in an unmodified host cell.

In some embodiments, the host cell natively comprises a nucleic acid encoding an enzyme capable of phenylacetaldehyde dehydrogenase into 3,4-dihydroxyphenyl acetate (3,4-DHPA), such as the enzyme phenylacetaldehyde dehydrogenase, wherein the host cell is reduced in the expression of the enzyme. When the host cell is *E. coli*, the enzyme is phenylacetaldehyde dehydrogenase encoded by the feaB gene. The reduced expression can be the result of a mutation that reduced expression or reduces enzymatic activity of the enzyme. An example of such a mutation is a truncated or deleted gene, such as a knock out mutation.

Any prokaryotic or eukaryotic host cell may be used in the present method so long as it remains viable after being transformed with a sequence of nucleic acids. Generally, although not necessarily, the host microorganism is bacterial. In some embodiments, the host cell is a Gram negative bacterium. In some embodiments, the host cell is of the phylum Proteobactera. In some embodiments, the host cell is of the class Gammaproteobacteria. In some embodiments, the host cell is of the order Enterobacteriales. In some embodiments, the host cell is of the family Enterobacteriaceae. Examples of bacterial host cells include, without limitation, those species assigned to the *Escherichia, Enterobacter, Azotobacter, Erwinia, Bacillus, Pseudomonas, Klebsielia, Proteus, Salmonella, Serratia, Shigella, Rhizobia, Vitreoscilla,* and *Paracoccus* taxonomical classes. Preferably, the host cell is not adversely affected by the transduction of the necessary nucleic acid sequences, the subsequent expression of the proteins (i.e., enzymes), or the resulting intermediates required for carrying out the steps associated with the mevalonate pathway. For example, it is preferred that minimal "cross-talk" (i.e., interference) occur between the host cell's own metabolic processes and those processes involved with the mevalonate pathway. Suitable eukaryotic cells include, but are not limited to, fungal, insect or mammalian cells. Suitable fungal cells are yeast cells, such as yeast cells of the *Saccharomyces* genus.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

The invention having been described, the following examples are offered to illustrate the subject invention by way of illustration, not by way of limitation.

EXAMPLE 1

Engineering of Hydroxytyrosol Production in *Escherichia coli*

Hydroxytyrosol (HTy) is one of the most powerful antioxidants with potential applications in industry, such as functional food, dietary supplement, cosmetics, and animal feed. An engineered *E. coli* capable of producing HTy with the synthetic pathway consists of five heterologous genes has been previously reported. Described herein are three metabolic engineering efforts to improve the efficiency of the synthetic HTy pathway.

First, the co-factor biosynthetic pathway for tyrosine hydroxylation is engineered. Next, inhibition of the tyrosine hydroxylation by downstream chemicals is identified and a co-culture strategy designed to overcome it is applied. With these engineering, the product yield from tyrosine is improve about 3-fold.

Lastly, a host strain is engineered to overproduce tyrosine. The production of L-DOPA from glucose without any external supplementation of tyrosine is confirmed, and the resulting L-DOPA is further converted into HTy by co-culture strategy with 25-fold improvement from the previous result.

A microbial HTy production process is engineered that has a potential for industrialization. Currently, HTy is produced from enriched olive extracts after chemical or enzymatic hydrolysis. There is an increasing demand for stable and sustainable production, and we believe microbial fermentation can be a promising solution.

Figure 3:
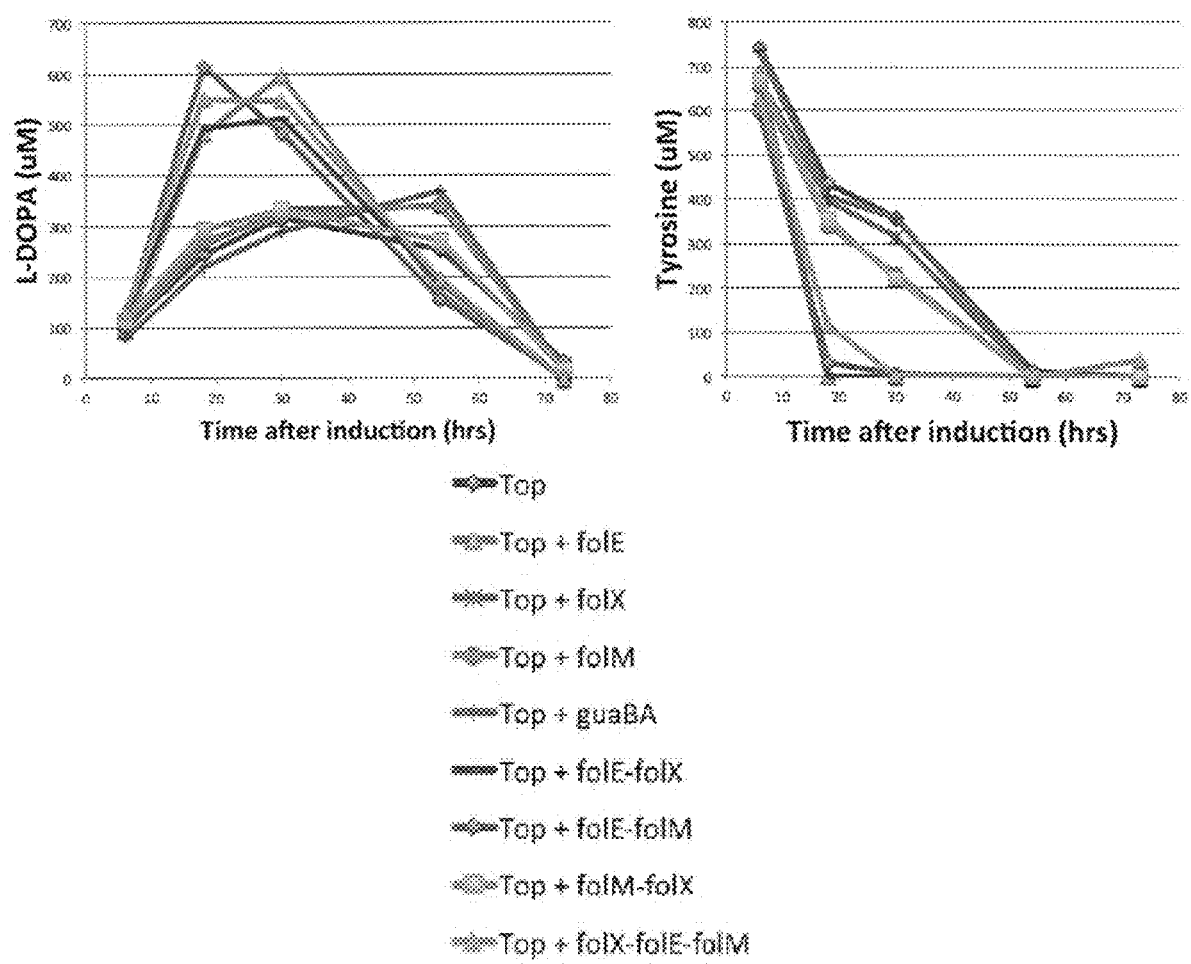
FIG. 3. JW1380 (feaB knock out), pBbE1k-TH-DHPR-PCD (top part), pBbS2c-(co-factor gene). Media M9Y (1 mM L-tyrosine, Ascorbic acid), 37 mL flask culture, Induction OD 0.5. Top part under pTrc (IPTG): 500 μM. Co-factor gene under pTet (aTc): 40 nM. Tyrosine and Ascorbic acid were supplemented at the induction. The supernatant is analyzed by LC-MS at 6, 18, 32 or 39, 53 hours after induction. Error bars indicate standard deviations from triplicate biological replicates.
Figure 4:
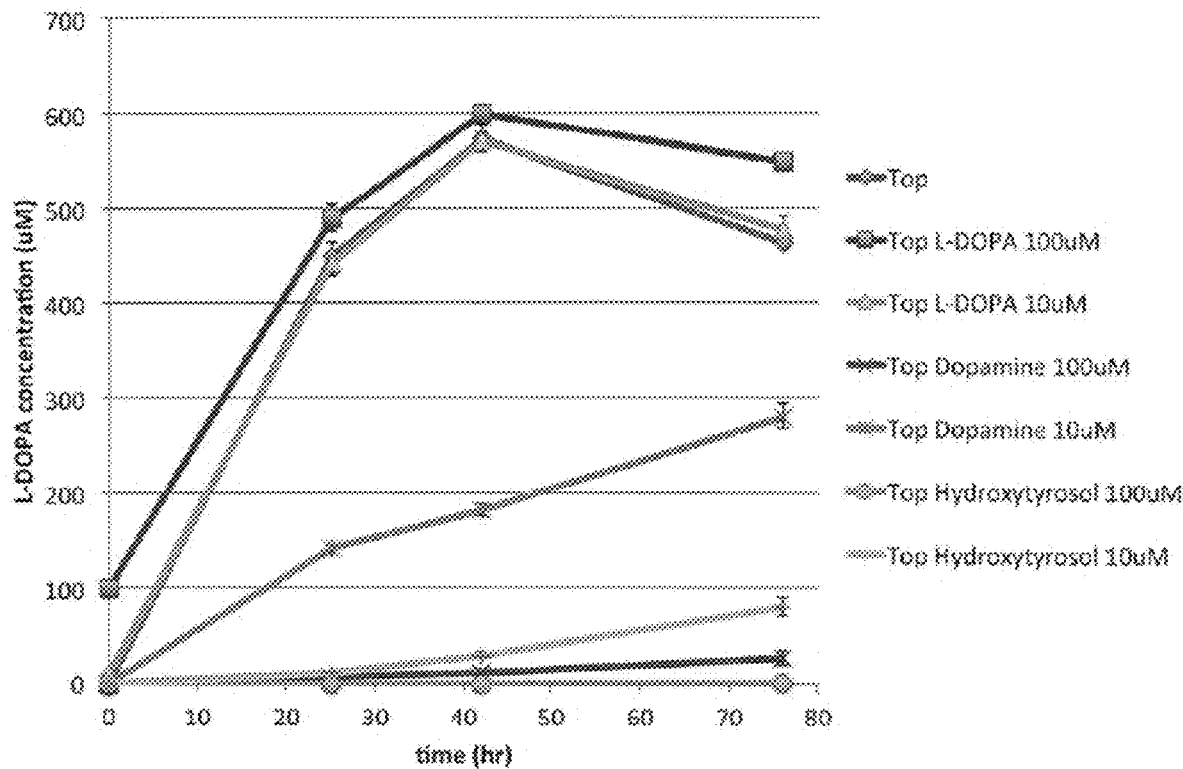
FIG. 4. Top: JW1380, pBbE1k-TH-reg, pBbS1a (empty vector). Media M9Y (1 mM L-tyrosine), 5 mL tube culture, Induction OD 0.4. Top part under pTrc (IPTG): 500 μM. Tyrosine or downstream chemical is supplemented at the induction. The supernatant is analyzed by LC-MS at 25, 42, 76 hours after induction. Error bars indicate standard deviations from triplicate biological replicates.
Figure 5A:
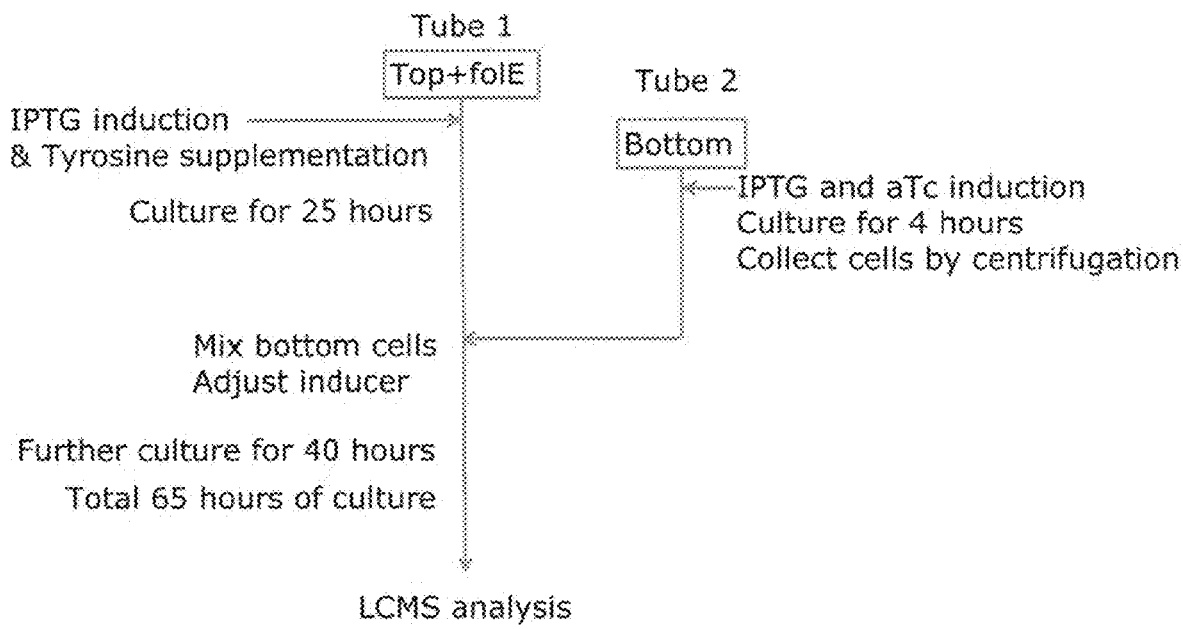
FIG. 5A. Co-culture scheme version 1 from tyrosine.
Figure 5B:
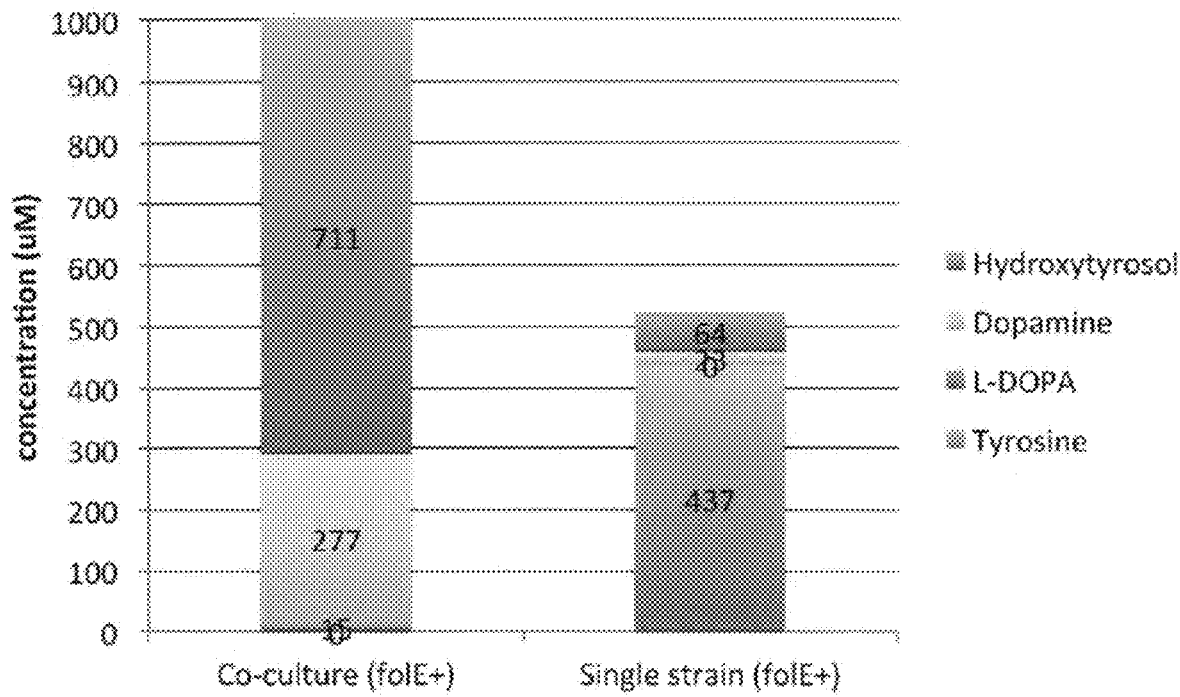
FIG. 5B. Products profile of co-culture from 1 mM tyrosine. Co-culture: Top-folE: JW1390, pBbE1k-TH-reg-folE, pBbS1a (empty vector). Bottom: JW1380, pBbE2k-TYO, pBbA1a-DDC-RFP. Bottom cells are collected 4 hours after induction, suspended with top strain and further cultured for 40 h (Total 65 h). Single strain: Top-folE+DDC-TYO: JW1380, pBbE1k-TH-reg-folE, pBbS1a-DDC-TYO. The supernatant is analyzed by LC-MS at 40 hours after induction.
Figure 6A:
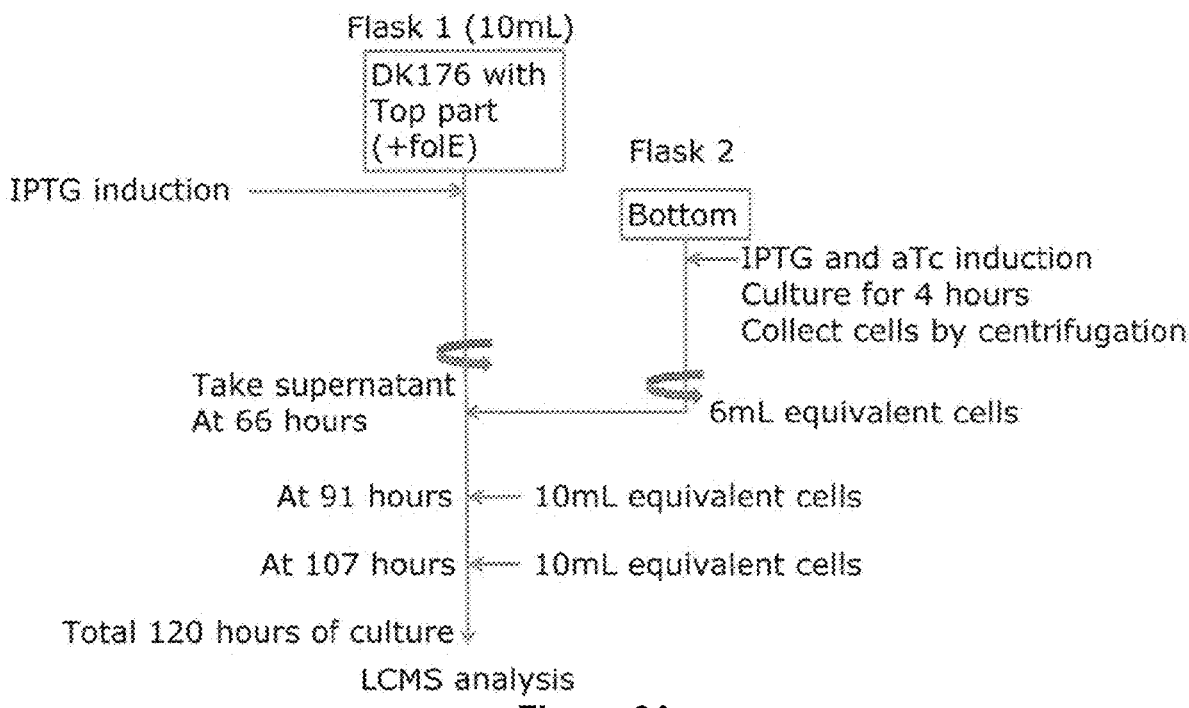
FIG. 6A. Co-culture scheme version 2 from glucose.
Figure 6B:
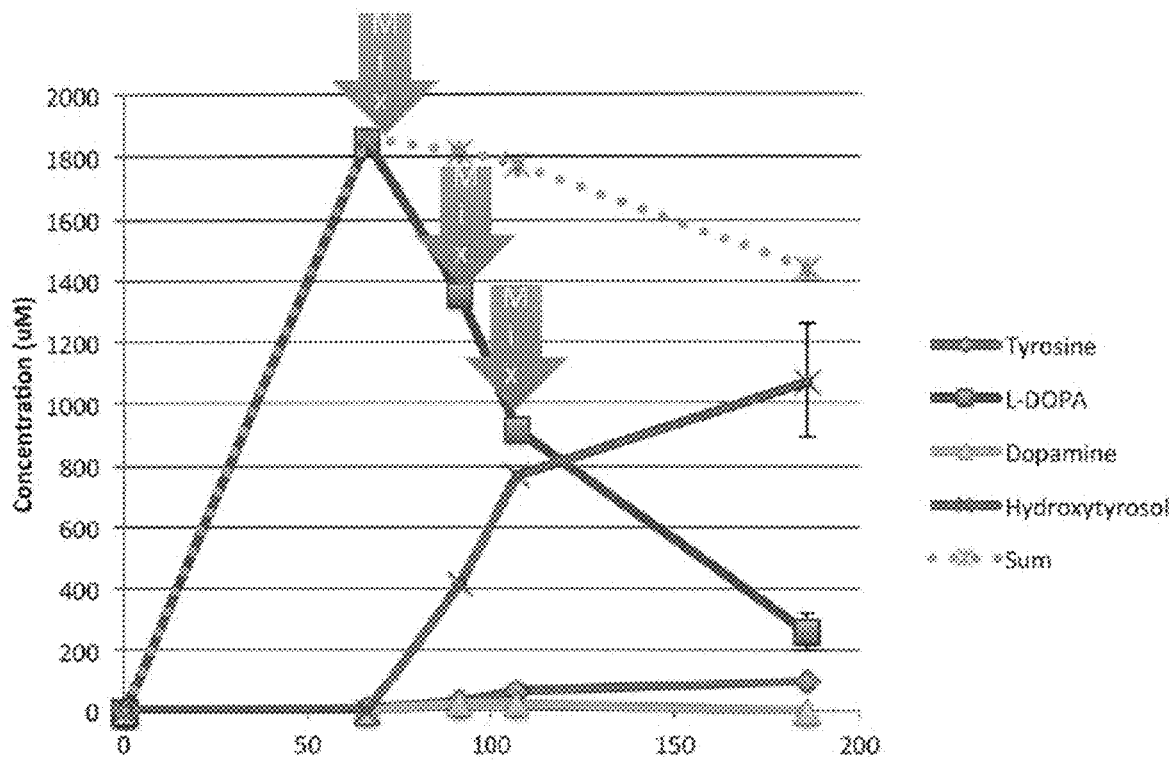
FIG. 6B. Products profile of co-culture from 5 g/L glucose. Top: DK176, pBbE1k-TH-reg-folE, pBbS1a (empty vector). Bottom: JW1380, pBbE2k-TYO, pBbA1a-DDC-RFP. Media M9Y (5 g/L glucose), 10 mL flask culture, induction OD 0.4.
Figure 7A:
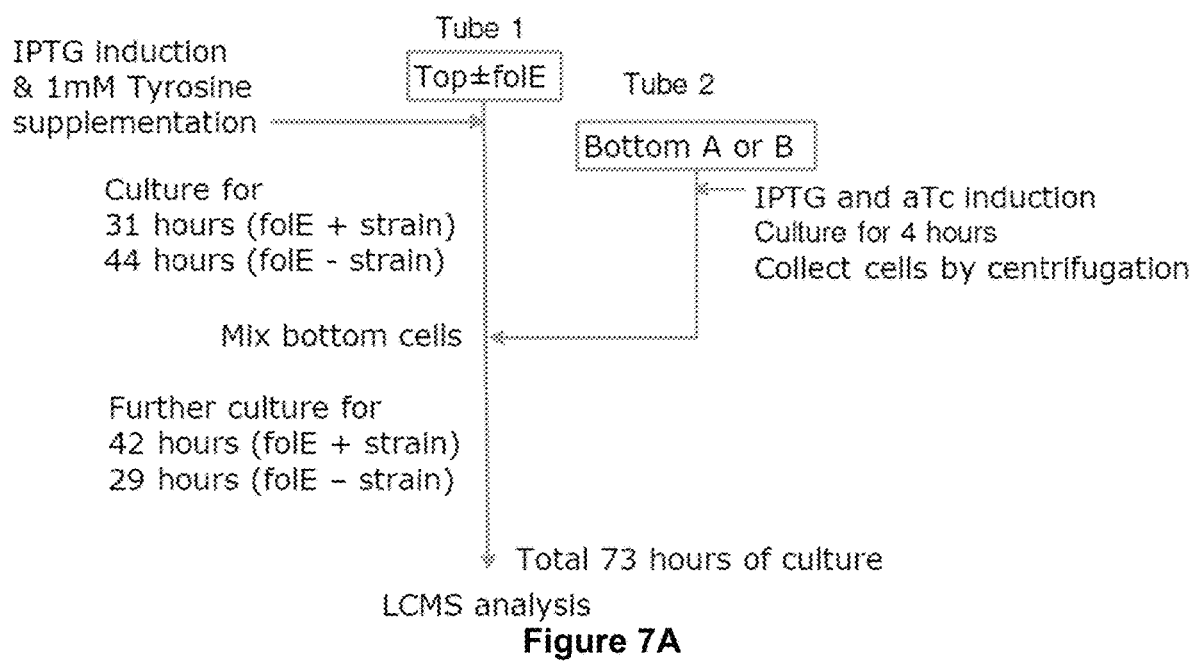
FIG. 7A. Co-culture scheme for HTy production (from Tyrosine).
Figure 7B:
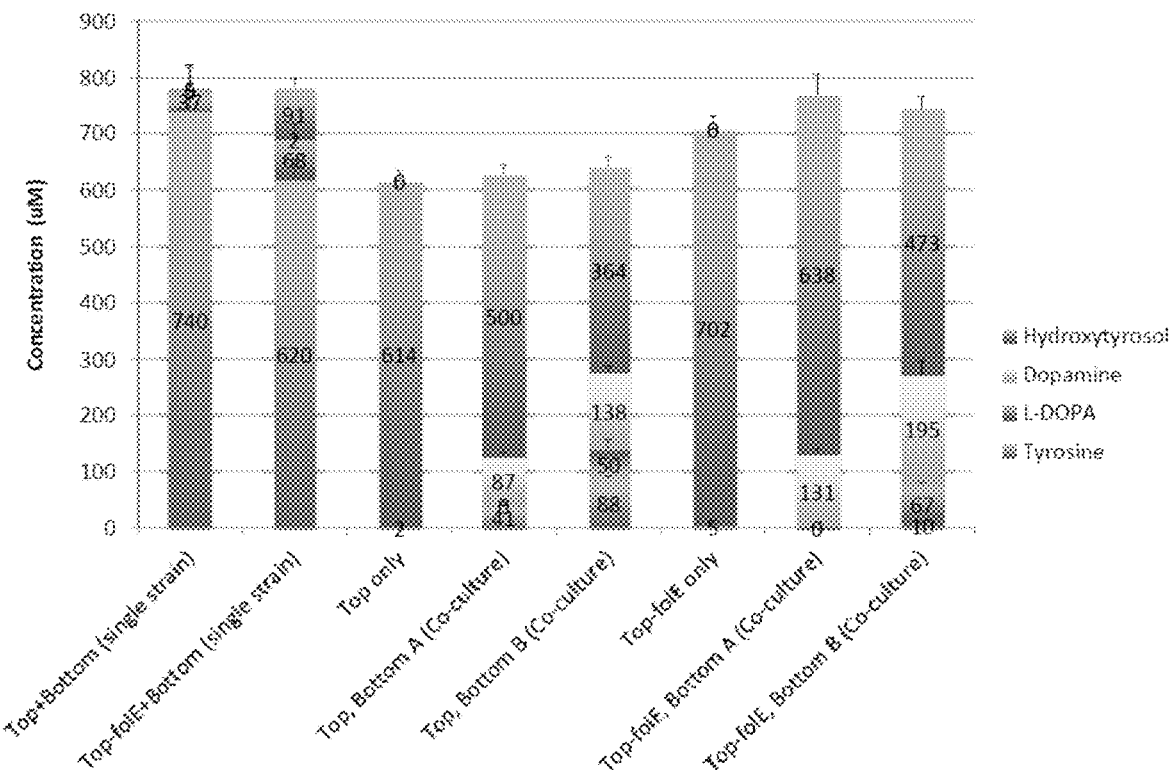
FIG. 7B. Products profile (single strain culture vs co-culture). Top+Bottom (single strain): JW1380, pBbE1k-TH-reg, pBbS1a-DDC-TYO. Top-folE+Bottom (single strain): JW1380, pBbE1k-TH-reg-folE, pBbS1a-DDC-TYO. Top: JW1380, pBbE1k-TH-reg, pBbS1a (empty vector). Top: JW1380, pBbE1k-TH-reg-folE, pBbS1a (empty vector). Bottom A: JW1380, pBbE2k-TYO, pBbA1a-DDC-RFP. Bottom B: JW1380, pBbS1a-DDC-TYO, pBbE1k (empty vector). Media M9Y (1 mM L-tyrosine), 5 mL tube culture, Induction OD 0.4. Top part under pTrc (IPTG): 500 μM. Tyrosine is supplemented at the induction. The supernatant is analyzed by LC-MS at 73 hours after induction. Error bars indicate standard deviations from triplicate biological replicates.
Figure 8A:
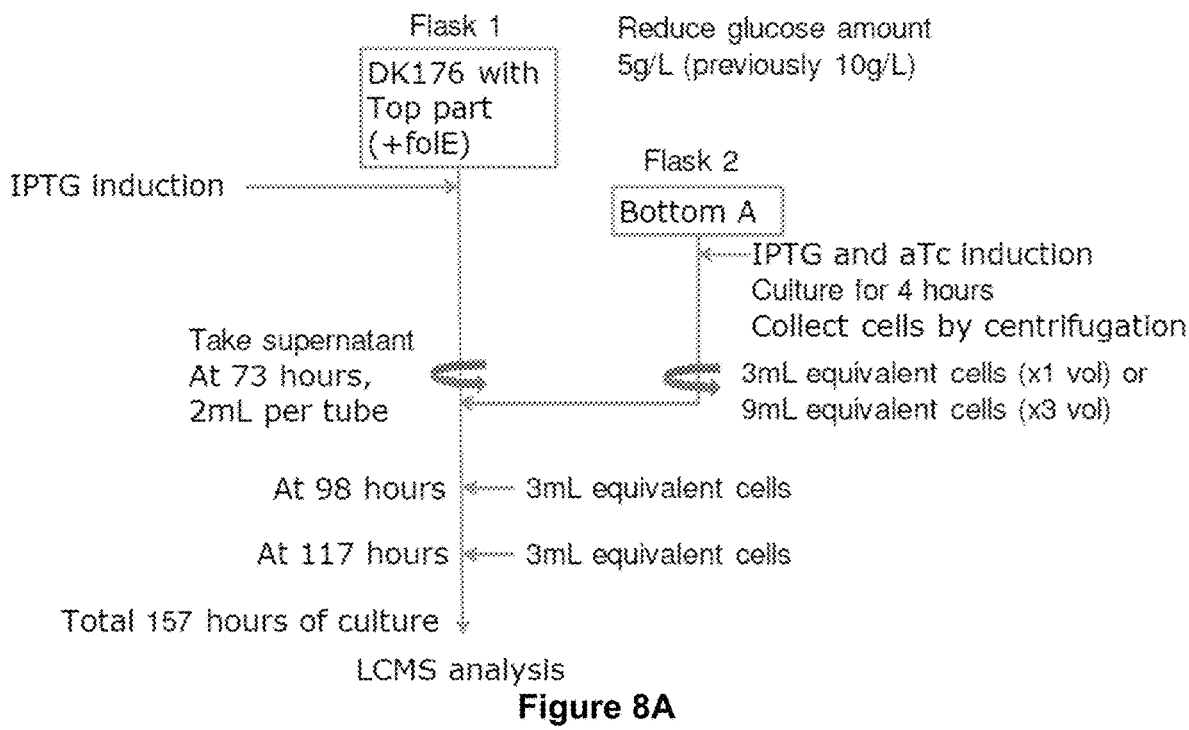
FIG. 8A. Co-culture scheme (from glucose).
Figure 8B:
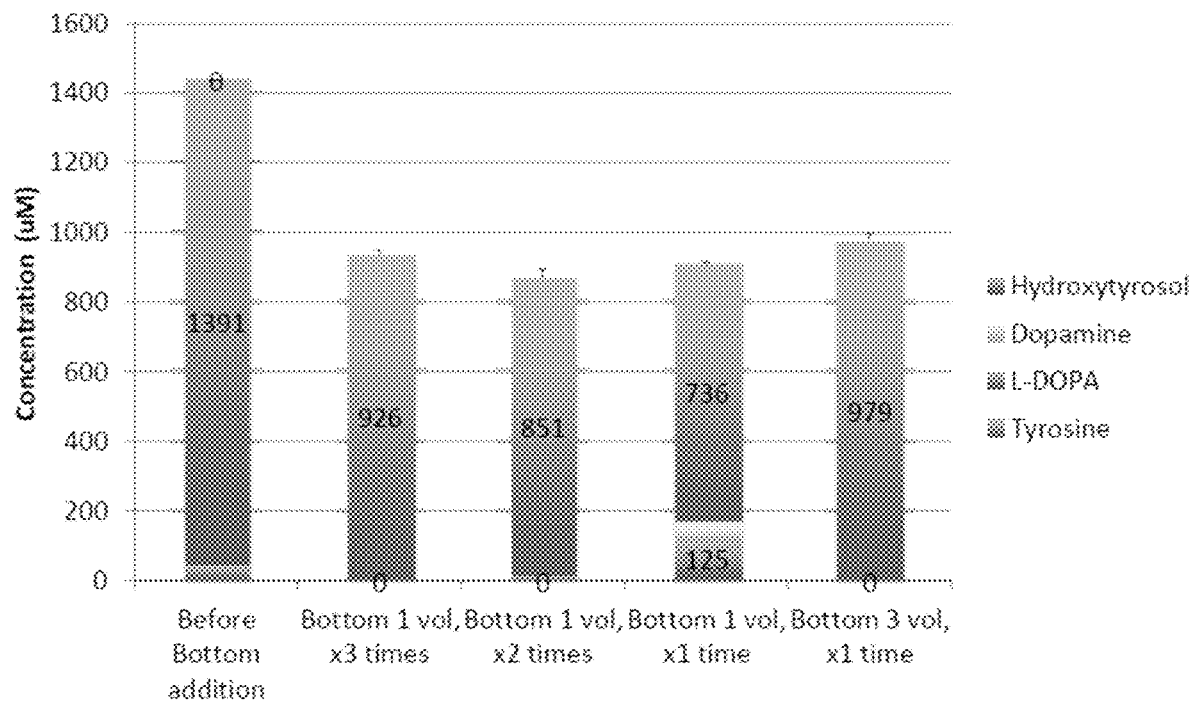
FIG. 8B. HTy production in co-culture from glucose. Top: DK176, pBbE1k-TH-reg-folE, pBbS1a (empty vector). Bottom A: JW1380, pBbE2k-TYO, pBbA1a-DDC-RFP. Media M9Y (5 g/L glucose). Error bars indicate standard deviations from triplicate biological replicates.
Figure 8C:
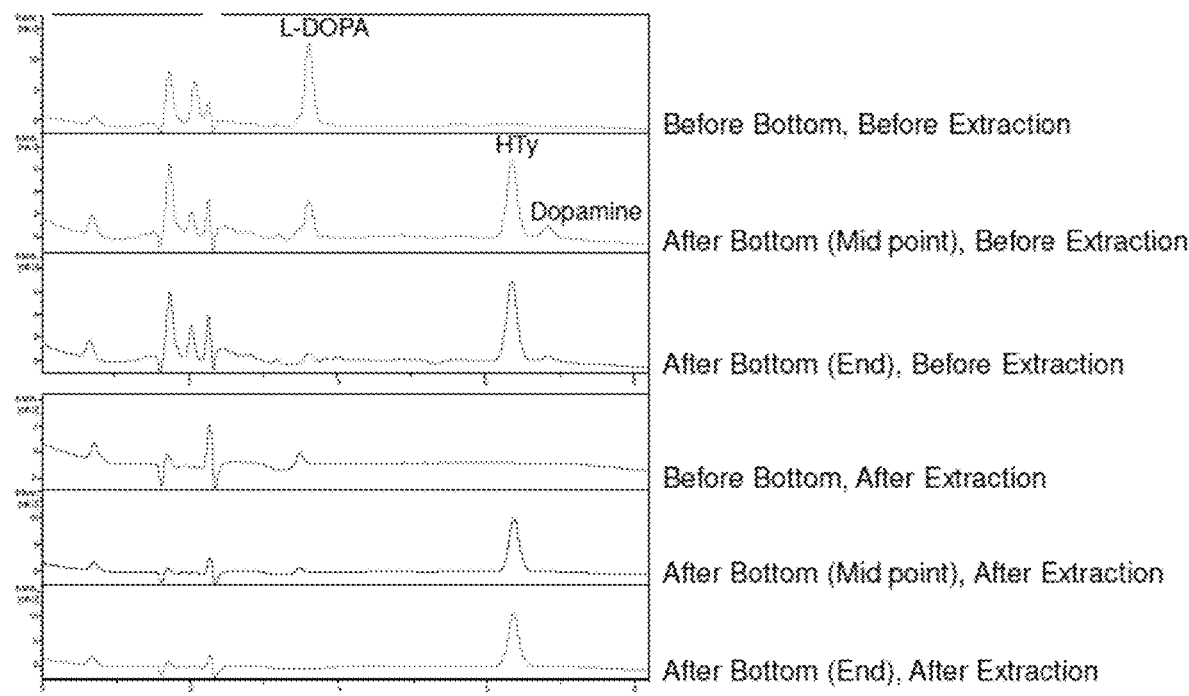
FIG. 8C. Simplified product profile by extraction with ethyl acetate. Supernatant at each time point is purified with ethyl acetate extraction.
Figure 9:
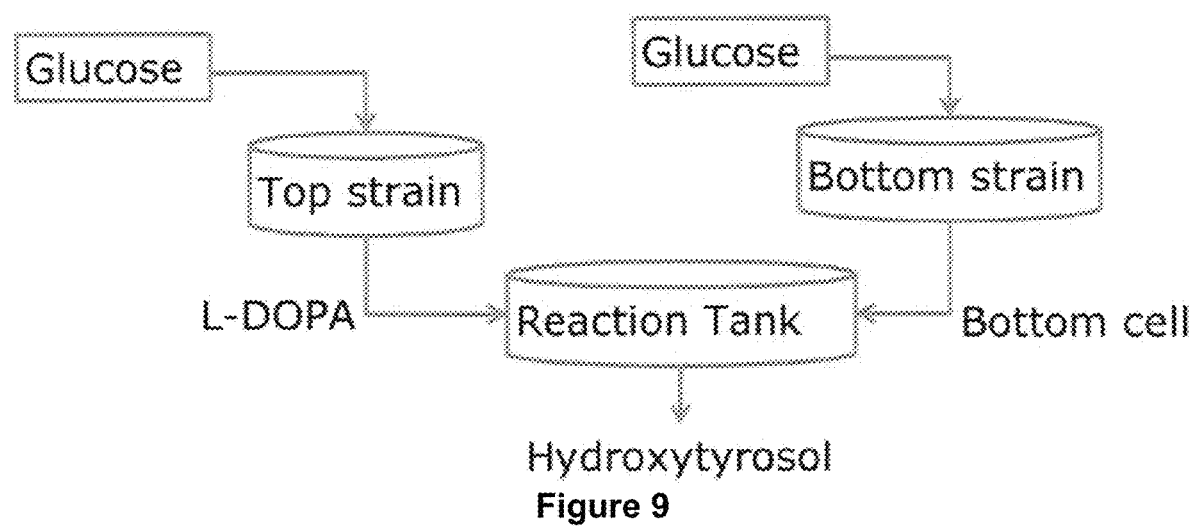
FIG. 9. Schematic drawing of industrial process.

FIG. 3 shows a co-factor biosynthetic pathway engineered for tyrosine hydroxylation. FIG. 3 shows FolE introduction increases L-DOPA production from tyrosine by 2-folds. Inhibition of the tyrosine hydroxylation by downstream compounds is identified (FIG. 4). FIG. 4 shows TH is inhibited by hydroxytyrosol and dopamine. By applying a co-culture strategy, the inhibition of the tyrosine hydroxylation by downstream compounds is overcome, and product yield from tyrosine is improve more than about 3-fold (FIG. 5). The gene expression of pathway enzymes is optimized using metabolomics and proteomic data. The host strain is engineered to overproduce tyrosine. With these modifications, the product from glucose is improved more than about 10-fold using the co-culture strategy (FIG. 6). HTy production increases more than 3-fold with the co-culture strategy shown in FIGS. 7A and 7B. FIGS. 8A to 8C show high purity HTy can be obtained from glucose.

This work demonstrates a potential industrial application of microbial HTy production and provides a good renewable microbial platform for the production of a wide range of chemicals that involve the hydroxylation of aromatic amino acid. Table 1 compares the previously reported hydroxytyrosol yields (Satoh et al. Metabolic Engineering 14 (2012) 603-610) and hydroxytyrosol yields reported herein.

TABLE 1

Comparison of previously reported hydroxytyrosol yields and hydroxytyrosol yields reported herein.

| Substrate (concentration in media) | Previously reported hydroxytyrosol yields (mM) | Hydroxytyrosol yields by co-culture reported herein by (mM) |
|---|---|---|
| L-DOPA (1 mM) | 0.74 | 0.74 |
| Tyrosine (1 mM) | 0.19 | 0.64 |
| Glucose (55 mM) | 0.08 | 0.98 |

EXAMPLE 2

Engineering of an *Escherichia Coli* L-tyrosine Overproducer

For some hydroxytyrosol producing strains, an L-tyrosine overproducer is required. Modular system for tyrosine producer is available (Juminaga et al., 2012), however, this system already utilizes two plasmids, thus making it difficult for combining with other modules. Instead of integrating full pathway for tyrosine biosynthesis, an L-tyrosine overproducer is constructed by integrating feedback resistant mutant tyrA (M53I;A354V) and aroG (D146N) at the pykF locus of *E. coli* MG1655 (DE3). AroG is located at the entrance of the shikimate pathway and tyrA is located at the very last reaction of the shikimate pathway for tyrosine synthesis. These two genes are known for being the first and second limiting reactions of tyrosine synthesis, thus enhancing these two genes is a good strategy for making a tyrosine overproducing strain. A strain, named DK176, is constructed by of introducing the aroG and tyrA genes into the parent strain. When the DK176 strain is cultured in M9Y medium (1% glucose), it achieves a yield of 2.68 mM of L-tyrosine, which is a significant improvement for L-tyrosine production.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

We claim:

1. A cell co-culture composition comprising a first *Escherichia coli* strain that produces levopdopa (L-DOPA); and a second *Escherichia coli* strain that converts L-DOPA produced by the first *Escherichia coli* strain into hydroxytyrosol (HTy), wherein the first *Escherichia coli* strain comprises a set of expression constructs to express the genes set forth in (a) not shared with the second strain and the second *Escherichia coli* strain comprises a set of expression constructs to express the genes set forth in (b) not shared with the first strain, wherein:

(a) the first *Escherichia coli* strain expresses endogenous FolE, FoIX, and FoIM genes and comprises: a first nucleic acid construct that expresses a mouse tyrosine hydroxylase (TH) comprising the amino acid sequence set forth in SEQ NO:1, or a variant thereof having TH activity that has at least 95% sequence identity to the amino acid sequence set forth in SEQ ID NO:1; a second nucleic acid construct that expresses a human dihydropteridine reductase (DHPR) comprising the amino acid sequence set forth in SEQ NO:3, or a variant thereof having DHPR activity that has at least 95% sequence identity to the amino acid sequence set forth in SEQ ID NO:3; and a third nucleic acid that expresses a human pterin-4-alpha-carbinolamine dehydratase (PCD) comprising the amino acid sequence set forth in SEQ NO:2, or a variant thereof having PCD activity that has at least 95% sequence identity to the amino acid sequence set forth in SEQ ID NO:2; and wherein each of the first, second, and third nucleic acid is operably linked to a promoter; and the first *Escherichia coli* strain further expresses the following enzymes for the synthesis of L-tyrosine:

(i) a feedback resistant mutant D146N of a DAHP synthase (AroG) having AroG activity that has at least 95% sequence identity to the amino acid sequence set forth in SEQ ID NO:7; and a feedback resistant mutant M53I A354V of a chorismate mutase/prephenate dehydrogenase (TryA) having TyrA activity and at least 95% sequence identity to the amino acid sequence set forth in SEQ ID NO:8; wherein a nucleic acid construct encoding the feedback resistant mutant D146N of the DAHP synthase and a nucleic acid construct encoding the feedback resistance mutant M53I A254V of the chorismate mutase/prephenate dehydrogenase are each operably linked to a promoter and integrated at the pykF locus; and (ii) phosphoenolpyruvate synthase (PpsA), transketolase A (TktA), DHQ synthase (AroB), DHQ dehydratase (AroD), quinate/shikimate dehydrogenase (YdiB), shikimate dehydrogenase (AroE), shikimate kinase I/II (AroK/L), EPSP synthase (AroA), chorismate synthase (AroC), and tyrosine aminotransferase (TyrB); and (b) the second *Escherichia coli* host cell strain is a strain in which the endogenous feaB gene is deleted, and comprises: a first nucleic acid construct that expresses a pig L-DOPA decarboxylase (DDC) comprising the amino acid sequence set forth in SEQ NO:5, or a variant thereof having DDC activity that has at least 95% sequence identity to the amino acid sequence set forth in SEQ ID NO:5; and a second nucleic acid construct that expresses a *Micrococcus luteus* monoamine oxidase (MAO) comprising the amino acid sequence set forth in SEQ ID NO:6, or a variant thereof having MAO activity that has at least 95% sequence identity to the amino acid sequence set forth in SEQ ID NO:6; wherein each of the first and second nucleic acid is operably linked to a promoter.

2. The cell co-culture composition of claim 1, wherein the first *Escherichia coli* strain produces 2.0 mM or more of L-tyrosine when grown or cultured in a M9Y defined medium (1% glucose).

3. The cell co-culture composition of claim 2, wherein the first *Escherichia coli* strain produces 2.6 mM or more of L-tyrosine when-grown or cultured in a M9Y defined medium (1% glucose).

4. A method for producing hydroxytyrosol (HTy) comprising:
culturing the cell co-culture composition of claim 1, wherein HTy is produced;
optionally extracting or separating the HTy from the co-culture.

5. The cell co-culture composition of claim 1, wherein the TH comprises the amino acid sequence set forth in SEQ ID NO:1; the DHPR comprises the amino acid sequence set forth in SEQ ID NO:3; the PCD comprises the amino acid sequence set forth in SEQ ID NO:2; the DDC comprises the amino acid sequence set forth in SEQ ID NO:5; and the MAO comprises the amino acid sequence set forth in SEQ ID NO:6.

6. The cell co-culture composition of claim 1, wherein the feedback resistant mutant D146N of the DAHP synthase comprises the amino acid sequence set forth in SEQ ID NO:7 and the feedback resistant mutant M531 A354V of the chorismate mutase/prephenate dehydrogenase comprises the amino acid sequence set forth in SEQ ID NO:8.

* * * * *